US00RE49432E

(19) United States
(12) Reissued Patent
Chin et al.

(10) Patent Number: US RE49,432 E
(45) **Date of Reissued Patent: *Feb. 28, 2023**

(54) SYSTEM AND METHOD FOR SPINAL IMPLANT PLACEMENT

(71) Applicant: Stryker European Operations Holdings LLC, Kalamazoo, MI (US)

(72) Inventors: Kingsley Richard Chin, Ft. Lauderdale, FL (US); T. Wade Fallin, Hyde Park, UT (US); Joshua A. Butters, Chandler, AZ (US); Daniel F. Justin, Orlando, FL (US)

(73) Assignee: Stryker European Operations Holdings LLC, Kalamazoo, MI (US)

( * ) Notice: This patent is subject to a terminal disclaimer.

(21) Appl. No.: 17/138,167

(22) Filed: Dec. 30, 2020

Related U.S. Patent Documents

Reissue of:
(64) Patent No.: 8,002,798
Issued: Aug. 23, 2011
Appl. No.: 11/202,487
Filed: Aug. 12, 2005

U.S. Applications:
(63) Continuation of application No. 16/384,315, filed on Apr. 15, 2019, now Pat. No. Re. 48,376, which is a
(Continued)

(51) Int. Cl.
*A61B 17/70* (2006.01)
*A61B 90/00* (2016.01)
(Continued)

(52) U.S. Cl.
CPC ..... *A61B 17/7083* (2013.01); *A61B 17/3201* (2013.01); *A61B 17/3417* (2013.01);
(Continued)

(58) Field of Classification Search
CPC . A61B 17/3417; A61B 19/00; A61B 17/7083; A61B 17/7091; A61B 17/7082;
(Continued)

(56) References Cited

U.S. PATENT DOCUMENTS 3,788,318 A 1/1974 Kim et al.
3,789,852 A 2/1974 Kim
(Continued)

FOREIGN PATENT DOCUMENTS

DE 3711091 10/1988
DE 4238339 A1 5/1994
(Continued)

OTHER PUBLICATIONS

Synthes; MIRA For M.LS.S, Surgical Technique Brochure. Synthes, p. 1-7, undated.
(Continued)

*Primary Examiner* — William C Doerrler
(74) *Attorney, Agent, or Firm* — Lerner, David, Littenberg, Krumholz & Mentlik, LLP

(57) ABSTRACT

A posterior spinal fusion system may include a plurality of cannulas that mate with cages polyaxially coupled to pedicle screws. The cannulas maintain access to the pedicle screws to facilitate percutaneous insertion of a fusion rod into engagement with the cages. Each cannula has a pair of blades that may be held together by an abutment member that at least partially encircles the blades. Each abutment member abuts the skin to define a variable subcutaneous length of the corresponding cannula. Each abutment members is also lockably removable from the corresponding blades to enable the blades to pivot with respect to the connecting element to a position in which they can be withdrawn from the connecting element. The blades of each cannula are spaced apart to provide first and second slots of each cannula, through which the fusion rod can be percutaneously inserted.

17 Claims, 24 Drawing Sheets

Related U.S. Application Data continuation of application No. 15/620,402, filed on Jun. 12, 2017, now Pat. No. Re. 47,348, which is a continuation of application No. 14/824,951, filed on Aug. 12, 2015, now Pat. No. Re. 46,432, which is a continuation of application No. 13/973,462, filed on Aug. 22, 2013, now Pat. No. Re. 45,676, which is a continuation of application No. 13/972,493, filed on Aug. 21, 2013, now Pat. No. Re. 45,338, which is an application for the reissue of Pat. No. 8,002,798, which is a continuation-in-part of application No. 10/868,075, filed on Jun. 15, 2004, now Pat. No. 7,955,355.

(60) Provisional application No. 60/682,783, filed on May 19, 2005, provisional application No. 60/518,580, filed on Nov. 8, 2003.

(51) Int. Cl.
*A61B 17/3201* (2006.01)
*A61B 17/34* (2006.01)
*A61B 17/00* (2006.01)

(52) U.S. Cl.
CPC ..... *A61B 17/7035* (2013.01); *A61B 17/7037* (2013.01); *A61B 17/7082* (2013.01); *A61B 17/7085* (2013.01); *A61B 17/7091* (2013.01); *A61B 90/00* (2016.02); *A61B 17/00234* (2013.01); *A61B 17/3421* (2013.01); *A61B 17/701* (2013.01); *A61B 17/7032* (2013.01); *A61B 90/39* (2016.02); *A61B 2017/00738* (2013.01); *A61B 2017/3443* (2013.01); *A61B 2017/3445* (2013.01); *A61B 2017/3492* (2013.01); *A61B 2090/036* (2016.02); *A61B 2090/037* (2016.02)

(58) Field of Classification Search
CPC ..... A61B 17/7035; A61B 17/7037; A61B 17/7085; A61B 17/3201; A61B 90/39; A61B 17/00738; A61B 2090/036; A61B 2090/037; A61B 17/3492; A61B 17/3421; A61B 17/701; A61B 17/7032; A61B 2017/3445; A61B 2017/3443
USPC ..... 606/246
See application file for complete search history.

(56) References Cited

U.S. PATENT DOCUMENTS 3,892,232 A 7/1975 Neufeld
4,269,184 A 5/1981 Montgomery
4,350,151 A 9/1982 Scott
4,409,968 A 10/1983 Drummond
4,411,259 A 10/1983 Drummond
4,448,191 A 5/1984 Rodnyansky et al.
4,449,532 A 5/1984 Storz et al.
4,545,374 A 10/1985 Jacobson
4,562,832 A 1/1986 Wilder
4,611,581 A 9/1986 Steffee
4,790,297 A 12/1988 Luque
4,817,587 A 4/1989 Janese
4,862,891 A 9/1989 Smith
4,899,729 A 2/1990 Gill
4,913,134 A 4/1990 Luque
4,984,564 A 1/1991 Yuen
5,010,879 A 4/1991 Moriya et al.
5,027,793 A 7/1991 Engelhardt
5,035,232 A 7/1991 Lutze
5,125,396 A 6/1992 Ray
5,139,487 A 8/1992 Baber
5,171,279 A 12/1992 Mathews
5,183,464 A 2/1993 Dubrul et al.
5,195,541 A 3/1993 Obenchain
5,197,971 A 3/1993 Bonutti
5,242,443 A 9/1993 Kambin
5,293,863 A 3/1994 Zhu
5,295,994 A 3/1994 Bonutti
D346,217 S 4/1994 Sparker et al.
5,312,417 A 5/1994 Wilk
5,357,983 A 10/1994 Mathews
5,377,667 A 1/1995 Patton
5,381,788 A 1/1995 Matula
5,395,317 A 3/1995 Kambin
5,409,488 A 4/1995 Ulrich
5,425,732 A 6/1995 Ulrich
5,439,464 A 8/1995 Shapiro
5,454,365 A 10/1995 Bonutti
5,464,011 A 11/1995 Bridge
5,480,440 A 1/1996 Kambin
5,496,322 A 3/1996 Mathews
5,545,228 A 8/1996 Kambin
5,569,248 A 10/1996 Mathews
5,569,290 A 10/1996 McAfee
5,584,887 A 12/1996 Kambin
5,601,562 A 2/1997 Wolf et al.
5,601,590 A 2/1997 Bonutti
5,707,359 A 1/1998 Bufalini
5,720,751 A 2/1998 Jackson
5,728,097 A 3/1998 Mathews
5,741,261 A 4/1998 Moskovitz
5,743,907 A 4/1998 Asher
5,746,720 A 5/1998 Stouder, Jr.
5,762,629 A 6/1998 Kambin
5,772,594 A 6/1998 Barrick
5,792,044 A 8/1998 Foley
5,795,289 A 8/1998 Wyttenbach
5,882,344 A 3/1999 Stouder, Jr.
5,885,291 A 3/1999 Moskovitz
5,885,292 A 3/1999 Moskovitz
5,891,147 A 4/1999 Moskovitz
5,902,231 A 5/1999 Foley
5,928,139 A 7/1999 Koros et al.
5,944,658 A 8/1999 Koros et al.
5,954,635 A 9/1999 Foley
5,957,888 A 9/1999 Hinchliffe
5,961,499 A 10/1999 Bonutti
5,964,761 A 10/1999 Kambin
5,976,146 A 11/1999 Ogawa et al.
6,007,487 A 12/1999 Foley
6,033,406 A 3/2000 Mathews
6,036,692 A 3/2000 Burel et al.
6,080,156 A 6/2000 Asher
6,127,597 A 10/2000 Beyar
6,152,871 A 11/2000 Foley
6,159,179 A 12/2000 Simonson
6,162,170 A 12/2000 Foley
6,175,758 B1 1/2001 Kambin
6,176,823 B1 1/2001 Foley et al.
6,183,472 B1 2/2001 Lutz
6,187,000 B1 2/2001 Davison
6,197,002 B1 3/2001 Peterson
6,200,322 B1 3/2001 Branch
6,206,822 B1 3/2001 Foley
6,206,826 B1 3/2001 Mathews
6,217,509 B1 4/2001 Foley
6,226,548 B1 5/2001 Foley et al.
6,235,028 B1 5/2001 Brumfield et al.
6,287,313 B1 9/2001 Sasso
6,338,730 B1 1/2002 Bonutti
6,358,266 B1 3/2002 Bonutti
6,371,968 B1 4/2002 Kogasaka
6,425,859 B1 7/2002 Foley
6,475,218 B2 11/2002 Gournay et al.
6,485,518 B1 11/2002 Cornwall
6,506,151 B2 1/2003 Estes
6,520,907 B1 2/2003 Foley et al.
6,524,320 B2 2/2003 DiPoto
6,530,926 B1 3/2003 Davison
6,530,929 B1 3/2003 Justis
6,558,386 B1 5/2003 Cragg

(56) References Cited

U.S. PATENT DOCUMENTS 6,558,390 B2 5/2003 Cragg
6,562,046 B2 5/2003 Sasso
6,575,979 B1 6/2003 Cragg
6,596,008 B1 7/2003 Kambin
6,605,095 B2 8/2003 Grossman
6,607,530 B1 8/2003 Carl et al.
6,613,050 B1 9/2003 Wagner
6,648,888 B1 11/2003 Shluzas
6,652,553 B2 11/2003 Davison
6,660,006 B2 * 12/2003 Markworth et al. ..... 606/86 A
6,692,434 B2 2/2004 Ritland
6,692,473 B2 2/2004 St. Cyr
6,723,095 B2 4/2004 Hammerslag
6,740,089 B2 5/2004 Haider
6,740,090 B1 5/2004 Cragg
6,746,449 B2 6/2004 Jones
6,749,614 B2 6/2004 Teitelbaum
6,770,074 B2 8/2004 Michelson
6,790,210 B1 9/2004 Cragg
6,793,656 B1 9/2004 Mathews
6,800,084 B2 10/2004 Davison
6,811,558 B2 11/2004 Davison
6,821,277 B2 11/2004 Teitelbaum
6,837,891 B2 1/2005 Davison
6,849,064 B2 2/2005 Hamada
6,923,811 B1 8/2005 Carl et al.
6,929,647 B2 8/2005 Cohen
7,011,660 B2 3/2006 Sherman et al.
7,083,621 B2 8/2006 Shaolian et al.
7,160,300 B2 1/2007 Jackson
7,250,052 B2 7/2007 Landry et al.
7,261,714 B2 8/2007 Richelsoph
7,282,064 B2 10/2007 Chin
7,306,603 B2 12/2007 Boehm, Jr. et al.
7,476,240 B2 1/2009 Raymond et al.
7,717,942 B2 5/2010 Schumacher
7,758,617 B2 7/2010 Iott et al.
7,811,288 B2 10/2010 Jones et al.
7,842,073 B2 11/2010 Richelsoph et al.
7,955,355 B2 6/2011 Chin
8,002,798 B2 8/2011 Chin et al.
8,105,361 B2 1/2012 Anderson et al.
8,177,817 B2 5/2012 Fallin
8,192,440 B2 6/2012 Jones et al.
8,894,655 B2 11/2014 Fallin et al.
RE45,338 E 1/2015 Chin et al.
RE45,676 E * 9/2015 Chin ..... A61B 17/3417
RE46,432 E * 6/2017 Chin ..... A61B 17/3417
RE47,348 E * 4/2019 Chin ..... A61B 17/7037
RE48,376 E * 1/2021 Chin ..... A61B 17/7082
2001/0011170 A1 8/2001 Davison et al.
2001/0027320 A1 10/2001 Sasso
2001/0029353 A1 10/2001 Peterson
2001/0049498 A1 12/2001 Davison et al.
2001/0049527 A1 12/2001 Cragg
2001/0053915 A1 12/2001 Grossman
2002/0016583 A1 2/2002 Cragg
2002/0045904 A1 4/2002 Fuss et al.
2002/0068975 A1 6/2002 Teitelbaum
2002/0082598 A1 6/2002 Teitelbaum
2002/0082600 A1 6/2002 Shaolian et al.
2002/0107519 A1 * 8/2002 Dixon et al. ..... 606/61
2002/0116006 A1 8/2002 Cohen
2002/0161368 A1 10/2002 Foley et al.
2002/0173796 A1 11/2002 Cragg
2002/0198526 A1 12/2002 Shaolian
2003/0004517 A1 1/2003 Anderson
2003/0060826 A1 3/2003 Foley et al.
2003/0073998 A1 4/2003 Pagliuca
2003/0083688 A1 5/2003 Simonson
2003/0139648 A1 7/2003 Foley
2003/0195518 A1 10/2003 Cragg
2003/0199871 A1 10/2003 Foley et al.
2003/0199872 A1 * 10/2003 Markworth et al. ..... 606/61
2003/0199884 A1 10/2003 Davison et al.
2003/0204189 A1 10/2003 Cragg
2003/0208202 A1 11/2003 Falahee
2003/0225408 A1 12/2003 Nichols et al.
2003/0229353 A1 12/2003 Cragg
2004/0006341 A1 1/2004 Shaolian
2004/0006344 A1 1/2004 Nguyen
2004/0034351 A1 2/2004 Sherman et al.
2004/0039384 A1 2/2004 Boehm
2004/0059333 A1 3/2004 Carl et al.
2004/0082954 A1 4/2004 Teitelbaum
2004/0082960 A1 4/2004 Davison
2004/0082961 A1 4/2004 Teitelbaum
2004/0087950 A1 5/2004 Teitelbaum
2004/0093001 A1 5/2004 Hamada
2004/0106934 A1 6/2004 Grossman
2004/0133201 A1 7/2004 Shluzas et al.
2004/0138662 A1 7/2004 Landry et al.
2004/0143265 A1 7/2004 Landry et al.
2004/0143268 A1 7/2004 Falahee
2004/0147928 A1 7/2004 Landry et al.
2004/0147936 A1 7/2004 Rosenberg et al.
2004/0162560 A1 8/2004 Raynor et al.
2004/0172022 A1 9/2004 Landry et al.
2004/0176763 A1 * 9/2004 Foley et al. ..... 606/60
2004/0194791 A1 10/2004 Sterman et al.
2004/0215190 A1 10/2004 Nguyen
2004/0215193 A1 10/2004 Shaolian et al.
2004/0236317 A1 11/2004 Davison
2004/0254576 A1 12/2004 Dunbar et al.
2005/0010220 A1 1/2005 Casutt et al.
2005/0010221 A1 1/2005 Dalton
2005/0021030 A1 1/2005 Pagliuca et al.
2005/0021031 A1 1/2005 Foley et al.
2005/0025771 A1 2/2005 Wagner et al.
2005/0033297 A1 2/2005 Davison
2005/0038432 A1 2/2005 Shaolian et al.
2005/0038434 A1 2/2005 Mathews
2005/0043741 A1 2/2005 Michelson
2005/0043742 A1 2/2005 Bruneau et al.
2005/0059969 A1 3/2005 McKinley
2005/0065515 A1 3/2005 Jahng
2005/0065517 A1 3/2005 Chin
2005/0070917 A1 3/2005 Justis
2005/0080418 A1 4/2005 Simonson et al.
2005/0085813 A1 4/2005 Spitler
2005/0090822 A1 4/2005 DiPoto
2005/0090833 A1 4/2005 DiPoto
2005/0113833 A1 5/2005 Davison
2005/0124991 A1 6/2005 Jahng
2005/0131407 A1 6/2005 Sicvol et al.
2005/0131408 A1 6/2005 Sicvol et al.
2005/0131421 A1 6/2005 Anderson et al.
2005/0131422 A1 6/2005 Anderson et al.
2005/0137461 A1 6/2005 Marchek et al.
2005/0137593 A1 6/2005 Gray et al.
2005/0149022 A1 7/2005 Shaolian et al.
2005/0149035 A1 7/2005 Pimenta et al.
2005/0154389 A1 * 7/2005 Selover et al. ..... 606/61
2005/0171540 A1 8/2005 Lim et al.
2005/0182410 A1 * 8/2005 Jackson ..... 606/73
2005/0192570 A1 9/2005 Jackson ..... A61B 17/7037 606/264
2005/0245928 A1 11/2005 Colleran et al.
2005/0251139 A1 * 11/2005 Roh ..... 606/61
2005/0277942 A1 12/2005 Kullas et al.
2006/0030839 A1 2/2006 Park et al.
2006/0036252 A1 * 2/2006 Baynham ..... A61B 17/7035 606/328
2006/0084980 A1 4/2006 Melkent et al.
2006/0111713 A1 * 5/2006 Jackson ..... 606/61
2006/0111714 A1 5/2006 Foley
2006/0200135 A1 9/2006 Sherman et al.
2006/0217735 A1 9/2006 MacDonald et al.
2006/0247630 A1 11/2006 Iott et al.
2006/0247658 A1 11/2006 Pond et al. ..... A61B 17/7082 606/104
2006/0264934 A1 11/2006 Fallin
2006/0293680 A1 12/2006 Jackson
2007/0043359 A1 2/2007 Altarac et al.

(56) References Cited

U.S. PATENT DOCUMENTS

| | | | |
|---|---|---|---|
| 2008/0009864 | A1 | 1/2008 | Forton et al. |
| 2009/0099605 | A1 | 4/2009 | Fallin et al. |
| 2009/0216328 | A1 | 8/2009 | Birkmeyer et al. |
| 2009/0228056 | A1 | 9/2009 | Jackson |
| 2010/0137915 | A1 | 6/2010 | Anderson et al. |
| 2010/0331901 | A1 | 12/2010 | Iott et al. |
| 2011/0015678 | A1 | 1/2011 | Jackson |
| 2011/0077692 | A1 | 3/2011 | Jackson |
| 2011/0152940 | A1 | 6/2011 | Frigg et al. |
| 2011/0238120 | A1 | 9/2011 | Chin |
| 2011/0245884 | A9 | 10/2011 | Brumfield et al. |
| 2012/0089191 | A1 | 4/2012 | Altarac et al. |
| 2012/0123477 | A1 | 5/2012 | Landry et al. |
| 2012/0158070 | A1 | 6/2012 | Jackson |
| 2012/0197302 | A1 | 8/2012 | Fallin |

FOREIGN PATENT DOCUMENTS

| | | | |
|---|---|---|---|
| DE | 29710979 | | 6/1997 |
| DE | 29710979 | U1 | 8/1997 |
| DE | 19726754 | | 2/1999 |
| DE | 19726754 | A1 | 2/1999 |
| DE | 10027988 | | 1/2002 |
| DE | 202004009073 | U1 | 8/2004 |
| DE | 202005007495 | U1 | 8/2005 |
| EP | 0528177 | | 2/1993 |
| EP | 0528562 | | 2/1993 |
| EP | 528562 | A2 | 2/1993 |
| EP | 0611116 | A1 | 8/1994 |
| EP | 0665731 | A1 | 8/1995 |
| EP | 611116 | B1 | 7/1996 |
| EP | 665731 | A4 | 1/1997 |
| EP | 1006888 | | 6/2000 |
| EP | 1006888 | A4 | 6/2000 |
| EP | 1027988 | | 8/2000 |
| EP | 1248568 | | 10/2002 |
| EP | 1248568 | B1 | 9/2003 |
| EP | 1374786 | | 1/2004 |
| EP | 1468652 | | 10/2004 |
| EP | 1468652 | A1 | 10/2004 |
| EP | 1545355 | | 6/2005 |
| SU | 839513 | | 6/1981 |
| SU | 839513 | A1 | 6/1981 |
| WO | 93/18722 | | 9/1993 |
| WO | 9409726 | A1 | 5/1994 |
| WO | WO-2004/238339 | | 5/1994 |
| WO | WO9409726 | A1 | 5/1994 |
| WO | 9514437 | | 6/1995 |
| WO | 97/14457 | | 4/1997 |
| WO | WO9714457 | A1 | 4/1997 |
| WO | 9822030 | A1 | 5/1998 |
| WO | 98/36785 | | 8/1998 |
| WO | WO9836785 | A1 | 8/1998 |
| WO | 98/38918 | | 9/1998 |
| WO | WO9838918 | A1 | 9/1998 |
| WO | 99/29242 | | 6/1999 |
| WO | WO9929242 | A1 | 6/1999 |
| WO | 99/51139 | | 10/1999 |
| WO | WO9951139 | A2 | 10/1999 |
| WO | 00/45720 | | 8/2000 |
| WO | WO0045720 | A1 | 8/2000 |
| WO | 01/012080 | | 2/2001 |
| WO | WO0112080 | A1 | 2/2001 |
| WO | 01/037744 | | 5/2001 |
| WO | WO0137744 | A2 | 5/2001 |
| WO | 0141681 | A1 | 6/2001 |
| WO | 01/056479 | | 8/2001 |
| WO | 01/060232 | | 8/2001 |
| WO | 01/060234 | | 8/2001 |
| WO | 01/060262 | | 8/2001 |
| WO | 01/060270 | | 8/2001 |
| WO | 2001060263 | | 8/2001 |
| WO | WO016270 | A1 | 8/2001 |
| WO | WO0156479 | A1 | 8/2001 |
| WO | WO0160232 | A3 | 8/2001 |
| WO | WO160234 | A2 | 8/2001 |
| WO | WO0160262 | A1 | 8/2001 |
| WO | WO0160263 | A1 | 8/2001 |
| WO | 01/095823 | | 12/2001 |
| WO | WO0195823 | A1 | 12/2001 |
| WO | 02/085217 | | 10/2002 |
| WO | WO016262 | C2 | 10/2002 |
| WO | WO02085217 | A2 | 10/2002 |
| WO | WO0160270 | C2 | 11/2002 |
| WO | 03020110 | | 3/2003 |
| WO | WO03020110 | A2 | 3/2003 |
| WO | 03028566 | | 4/2003 |
| WO | 03/037170 | | 5/2003 |
| WO | WO03037170 | A2 | 5/2003 |
| WO | 03/057055 | | 7/2003 |
| WO | WO03057055 | A1 | 7/2003 |
| WO | 03/079914 | | 10/2003 |
| WO | 03/088810 | | 10/2003 |
| WO | 03/088878 | | 10/2003 |
| WO | WO03079914 | A1 | 10/2003 |
| WO | WO03088810 | A2 | 10/2003 |
| WO | WO03088878 | A1 | 10/2003 |
| WO | 04004584 | | 1/2004 |
| WO | WO2004004584 | A1 | 1/2004 |
| WO | 04017847 | | 3/2004 |
| WO | 04021899 | A1 | 3/2004 |
| WO | WO2004017847 | A2 | 3/2004 |
| WO | WO2004021899 | A1 | 3/2004 |
| WO | 04/028382 | | 4/2004 |
| WO | WO2004028382 | A2 | 4/2004 |
| WO | 04/037070 | | 5/2004 |
| WO | 04037074 | A2 | 5/2004 |
| WO | 04041100 | A1 | 5/2004 |
| WO | WO-2004/041100 | | 5/2004 |
| WO | WO2004037070 | A2 | 5/2004 |
| WO | WO2004037074 | A2 | 5/2004 |
| WO | 2004058045 | | 7/2004 |
| WO | WO2004058045 | A2 | 7/2004 |
| WO | 04080318 | A1 | 9/2004 |
| WO | WO2004080318 | A1 | 9/2004 |
| WO | 05018466 | A2 | 3/2005 |
| WO | 05023123 | A1 | 3/2005 |
| WO | WO2005018466 | A2 | 3/2005 |
| WO | WO2005023123 | A1 | 3/2005 |
| WO | 05032358 | | 4/2005 |
| WO | 05060534 | A2 | 7/2005 |
| WO | WO-2005/060534 | A | 7/2005 |
| WO | 05072081 | | 8/2005 |
| WO | 2006116662 | A1 | 11/2006 |
| WO | WO-2006/116662 | | 11/2006 |

OTHER PUBLICATIONS

Encore Spine; Degenerative System, Encore Surgical Product Brochure, p. 1-6, Oct. 2002.

Bare Bones; Monthly Executive Summary, vol. 12, No. 1, p. 1-4, Jan. 2003.

Sofamor Danek; Sextant CD Horizon Sextant Rod Insertion System, Surgical Technique, Techniques, p. 1-29, 2003.

Sofamor Danek; Eclipse CD Horizon Eclipse Implants and Instruments, Information from the Sofamor Danek Web page, p. 1-3, printed Mar. 29, 2005.

Sofamor Danek; Metrx, X-Tube, Refraction System; Sofamor Danek Web page information p. 1-2, printed Mar. 29, 2005.

Smith and Nephew; 6.5mm and 4.0mm Cannulated Screws, Surgical Technique, p. 1-24, 1998.

Nuvasive; SpheRx DBR Minimally Disruptive Fixation, Nuvasive web page information, undated.

Spinal Concepts; Access Dilation Port, Spinal Concepts Web Page information 2 pages, downloaded Mar. 16, 2005, http://www.spinalconcepts.com/products/adp.html.

Charles Hartjen; The Atavi System, Surgical Technique Brochure. Endius, p. 1-17, undated.

Maxcess; Decompression Surgical Technique. Nuvasive Creative Spine Technology Product Brochure, p. 1-16, undated.

(56) References Cited

OTHER PUBLICATIONS

Pathfinder; Minimally invasive Spinal Fixation System and Surgical Technique. Spinal Concepts Product Brochure, p. 1-26, undated.
Pathfinder; Minimally Invasive Pedicie Fixation System. Spinal Concepts Product Brochure p. 1-4, May 2003.
Leu et al., Percutaneous Fusion of the Lumbar Spine, State of the Art Reviews, vol. 6, No. 3, pp. 593-604, Sep. 1992.
Kambin, Arthroscopic Lumbar Intervertebral Fusion, Chapter 95, The Adult Spine, vol. 2, pp. 2037-2046, Jan. 1997.
Kambin et al., Anterior Column Support for Failed Fusion, Revision Spine Surgery, pp. 589-600, published Jan. 1999.
Kambin, The Role of Minimally Invasive Surgery in Spinal Disorders, Advance Operative Orthopedics, vol. 3, pp. 147-171, Dec. 1994.
Kambin, "Arthroscopic Microdiscectomy", The Journal of Arthroscopy, vol. 8, No. 3, pp. 287-295, Sep. 1992.
Kambin et al., "Percutaneous Posterolateral Lumbar Discectomy and Decompression with a 6.9-millimeter cannula", The Journal of Bone and Joint Surgery, pp. 822-831, Jul. 1991.
Kambin, "Arthroscopic Microdiskectomy", The Mount Sinai Journal of Medicine, vol. 58, No. 2, Mar. 1991, pp. 159-164.
Kambin, "Posterolateral Percutaneous suction-excision of herniated lumbar intervertebral discs", Clinical Orthopaedics and Related Research. No 207, pp. 37-42, Jun. 1988.
Kambin, Posterolateral Percutaneous Lumbar Interbody Fusion, Arthroscopic Microdiscectomy, pp. 117-121, Jan. 1991.
Kambin, Posterolateral Percutaneous Lumbar Discectomy and Decompression Arthroscopic Microdiscectomy, Section IV. pp. 67-100, Jan. 1991.
Maxcess; XLIF 90° Surgical Technique. Nuvasive Creative Spine Technology Product Brochure, p. 1-26, 2005.
Office Action from U.S. Appl. No. 11/202,487, dated Dec. 9, 2008.
U.S. Appl. No. 11/202,487, filed Aug. 12, 2005.
Moss Miami Surgical Texhnique, DePuy, 14 pages, 1998.
Nex-Link; Spinal Fixation System, Spinal Concepts Web Page information, 1 page, "(retrieved Mar. 25, 2005)".
Sofamor Danek; Sextant CD Horizon Sextant Rod Insertion System, Sofamor Danek Web page, undated.
European Search Report for Application No. EP17160251 dated Jun. 7, 2017.
Extended European Search Report for Application No. 20200062.6, dated Apr. 1, 2021, 9 pages.
Pathfinder; *Minimally invasive Spinal Fixation System and Surgical Technique*. Spinal Concepts Product Brochure, p. 1-26.
Pathfinder; *Minimally Invasive Pedicle Fixation System*. Spinal Concepts Product Brochure p. 1-4.
Kambin, The Role of Minimally Invasive Surgery in Spinal Disorders, Advance Operative Orthopedics, vol. 3, pp. 147-171, 1995.
Kambin, Minimally Invasive Techniques in Spinal Surgery Current Practice, Neurosurgical Focus, wwwspineuniversecom, 16 pages, printed Aug. 24, 2005.
Diapason, Surgical Texchnique Catalog, Diapasan Spinal System, Jan. 2002.
Office Action from U.S. Appl. No. 11/526,785, dated Jan. 8, 2009.
Office Action from U.S. Appl. No. 10/868,075, dated Sep. 18, 2008.
U.S. Appl. No. 11/526,785, filed Sep. 25, 2006.
U.S. Appl. No. 12/316,637, filed Dec. 15, 2008.

* cited by examiner

SYSTEM AND METHOD FOR SPINAL IMPLANT PLACEMENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

[This] *Notice: More than one reissue application has been filed for the reissue of U.S. Pat. No. 8,002,798. The reissue applications are U.S. application Ser. No. 16/384,315, U.S. application Ser. No. 15/620,402, U.S. application Ser. No. 14/824,951, U.S. application Ser. No. 13/973,462, U.S. application Ser. No. 13/972,493, and the present application. The present* application *is a continuation reissue of U.S. application Ser. No. 16/384,315, filed on Apr. 15, 2019, which is a continuation reissue of U.S. application Ser. No. 15/620,402, filed on Jun. 12, 2017, which is a continuation reissue of U.S. application Ser. No. 14/824,951, filed on Aug. 12, 2015, which is a continuation reissue of U.S. application Ser. No. 13/973,462, filed on Aug. 22, 2013, which is a continuation reissue of U.S. application Ser. No. 13/972,493, filed on Aug. 21, 2013, which is an application for reissue of U.S. Pat. No. 8,002,798, which* is a continuation-in-part of U.S. application Ser. No. 10/868,075, filed on Jun. 15, 2004, which claims the [benefir] *benefit* of U.S. Provisional Application No. 60/518,580, filed Nov. 8, 2003, the [disclosure] *disclosures* of which are incorporated herein by reference. [This application claim] *U.S. Pat. No. 8,002,798 claims* the benefit of U.S. Provisional Application No. 60/682,783, filed on May 19, 2005, the disclosure of which is incorporated herein by reference.

This application relates to U.S. Application Ser. No. 10/669,927, filed on Sep. 24, 2003, the disclosure of which is hereby incorporated herein by reference.

BACKGROUND OF THE INVENTION

1. The Field of the Invention

The present invention relates generally to implantable devices, and more precisely, to posterior spinal fusion systems.

2. The Relevant Technology

Many people experience joint pain in one form or another. In particular, back pain may result from the occurrence of a wide variety of spinal pathologies. Some such pathologies are currently treated by fusing adjacent vertebrae to prevent their relative motion. According to one known method, pedicle screws are implanted in the pedicles and are rigidly secured to a rod passing posterior to the pedicles.

Unfortunately, current procedures often involve the exposure of a relatively large area to permit implantation of the rod. Some current procedures cannot be used to implant a rod that secures more than two vertebrae together. Other known procedures are somewhat complex, and therefore require many parts and surgical steps. Accordingly, there is a need for new fusion rod implantation systems and methods that remedy the shortcomings of the prior art.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to systems and methods for implantation of orthopedic devices. Although the examples provided herein generally relate to insertion of a rod for a posterior spinal fusion system, the present invention may be applied to any procedure in which a device is to be implanted in the body in a minimally invasive manner. Accordingly, the scope of the present invention is not intended to be limited by the examples discussed herein, but only by the appended claims.

As used herein, a "cannula" is an elongated structure having a hollow interior that provides communication between opposite ends of the elongated structure. A "subcutaneous length" is the portion of an object that lies below the surface of a patient's skin. "Transverse" refers to an object or direction that is not parallel with, and not nearly parallel with, another object or direction. A "connecting element" is any man-made structure that is implantable to remain in the body, and is connectable to an anatomic feature and/or another implantable structure. The term "percutaneous" refers to an action carried out at least partially underneath unbroken skin.

The term "discrete" refers to parts that are not formed as a single piece, but are separate pieces from each other. The term "coupled" refers to two elements that are secured together, whether they have been formed separately and secured together via a secondary operation, or they have been formed as a single piece (i.e., formed in a coupled state). The term "securable" refers to elements that are capable of being coupled together, or are already coupled together. A "blade" is an elongated, thin structure. "Polyaxial motion" refers to motion along or about multiple orthogonal axes.

Figure 1:
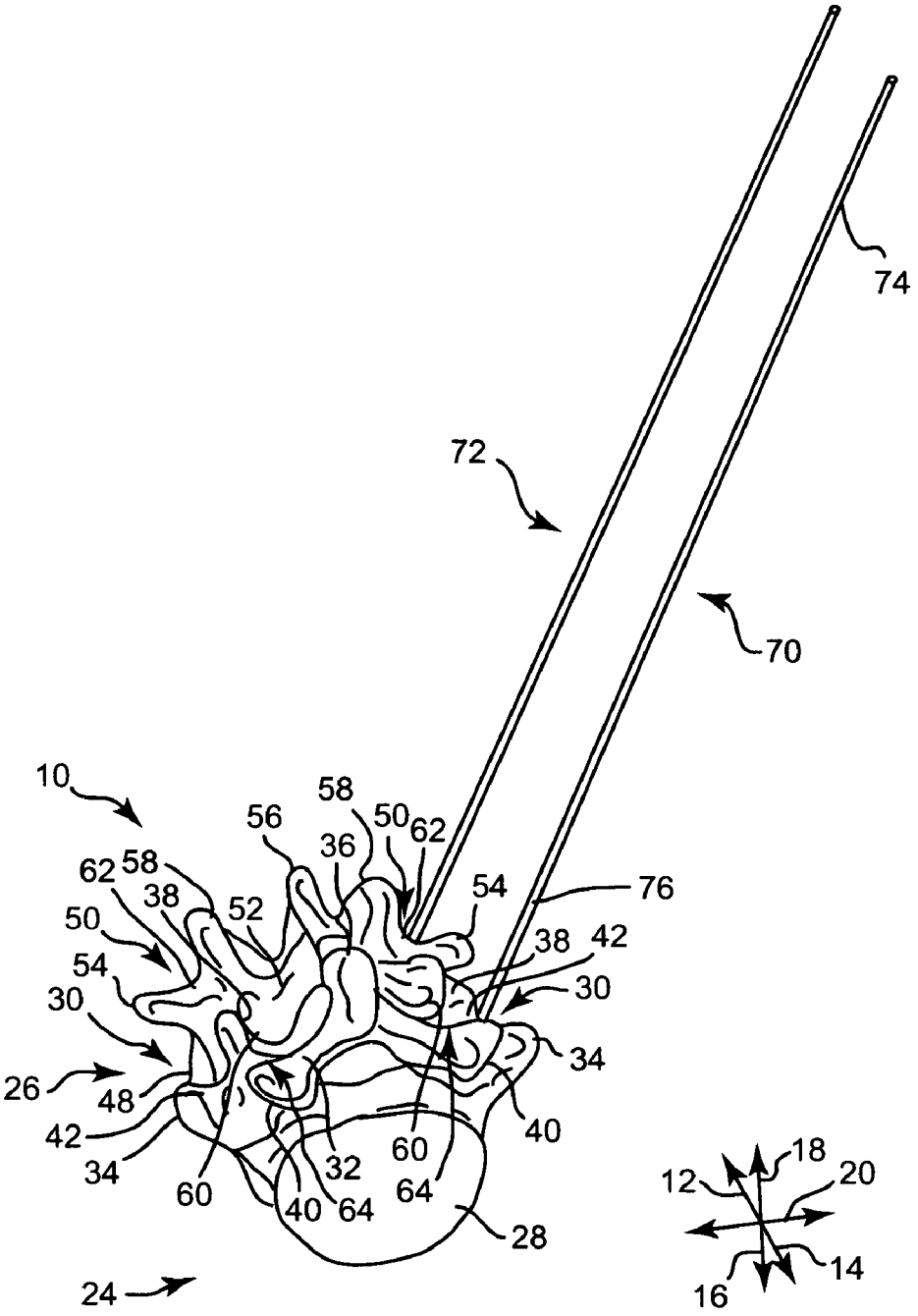
FIG. 1 is a perspective view of two adjacent vertebrae of a spine, with guide wires implanted in the pedicles of the right side.

Referring to FIG. 1, a perspective view illustrates a portion of a spine 10. FIG. 1 illustrates only the bony structures; accordingly, ligaments, cartilage, and other soft tissues are omitted for clarity. The spine 10 has a cephalad direction 12, a caudal direction 14, an anterior direction 16, a posterior direction 18, and a medial/lateral axis 20, all of which are oriented as shown by the arrows bearing the same reference numerals. In this application, "left" and "right" are used with reference to a posterior view, i.e., a view from behind the spine 10. "Medial" refers to a position or orientation toward a sagittal plane (i.e., plane of symmetry that separates left and right sides from each other) of the spine 10, and "lateral" refers to a position or orientation relatively further from the sagittal plane.

As shown, the portion of the spine 10 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods may be applicable to any vertebra or vertebrae of the spine 10 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. A posterior arch, or lamina 32, extends between the posterior ends of the pedicles 30 to couple the pedicles 30 together. The first vertebra 24 also has a pair of transverse processes 34 that extend laterally from the pedicles 30 generally along the medial/lateral axis 20, and a spinous process 36 that extends from the lamina 32 along the posterior direction 18.

The first vertebra 24 also has a pair of superior facets 38, which are positioned toward the top of the first vertebra 24 and face generally medially. Additionally, the first vertebra 24 has inferior facets 40, which are positioned toward the bottom of the first vertebra 24 and face generally laterally. Each of the pedicles 30 of the first vertebra 24 has a saddle point 42, which is positioned generally at the center of the juncture of each superior facet 38 with the adjacent transverse process 34.

Similarly, the second vertebra 26 has a body 48 from which two pedicles 50 extend posteriorly. A posterior arch, or lamina 52, extends between the posterior ends of the pedicles 50 to couple the pedicles 50 together. The second vertebra 26 also has a pair of transverse processes 54, each of which extends from the corresponding pedicle 50 generally along the medial/lateral axis 20, and a spinous process 56 that extends from the lamina 52 along the posterior direction 18.

The second vertebra 26 also has a pair of superior facets 58, which are positioned toward the top of the second vertebra 26 and face generally inward. Additionally, the second vertebra 26 has inferior facets 60, which are positioned toward the bottom of the second vertebra 26 and face generally outward. Each of the pedicles 60 of the second vertebra 26 has a saddle point 62, which is positioned generally at the center of the juncture of each superior facet 58 with the adjacent transverse process 54.

The superior facets 38 of the first vertebra 24 articulate (i.e., slide and/or press) with the inferior facets 60 of the second vertebra 26 to limit relative motion between the first and second vertebrae 24, 26. Thus, the combination of each superior facet 38 with the adjacent inferior facet 60 provides a facet joint 64. The first and second vertebrae 24, 26 thus define two facet joints 64 that span the distance between the first and second vertebrae 24, 26. The inferior facets 40 of the first vertebra 40 and the superior facets 58 of the second vertebra 26 are part of other facet joints that control motion between the first and second vertebrae 24, 26 and adjacent vertebrae (not shown) and/or the sacrum (also not shown).

The vertebrae 24, 26 and/or the intervertebral disc (not shown) between them, may be damaged or diseased in some manner that makes it desirable to secure the vertebrae 24, 26 together in a manner that prevents relative motion between them. Accordingly, posterior spinal fusion may be employed to secure the pedicles 30, 50 together. FIGS. 1 through 23 illustrate one system and method for installing a posterior spinal fusion system. FIG. 24 illustrates a cannula and cage according to one alternative embodiment of the invention.

As further illustrated in FIG. 1, a first guide wire 70 has been inserted into the right-side pedicle 30 of the first vertebra 24, and a second guide wire 72 has been inserted into the right-side pedicle 50 of the second vertebra 26. The guide wires 70, 72 pass through the saddle points 42, 62, respectively, of the pedicles 30, 50. Each of the guide wires 70, 72 has a proximal end 74 and a distal end 76. As shown, the proximal ends 74 are exposed, and the distal ends 76 are implanted in the pedicles 30, 50. The distal ends 76 may be implanted by methods known in the surgical arts.

Figure 2:
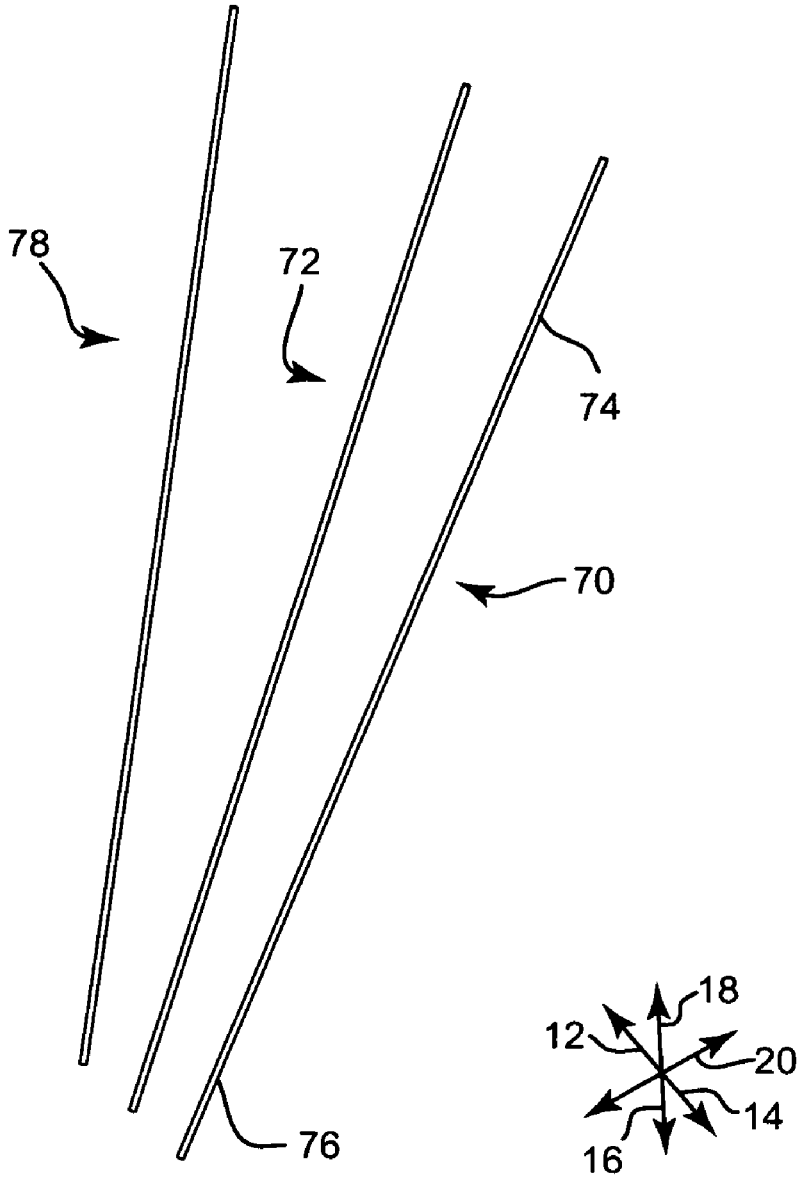
FIG. 2 is a perspective view of three guide wires in isolation, positioned as though implanted in the pedicles of the right sides of three adjacent vertebrae.

Referring to FIG. 2, a perspective view illustrates the first and second guide wires 70, 72 of FIG. 1, with the vertebrae 24, 26 removed for clarity. A third guide wire 78 is also shown. The third guide wire 78 is positioned adjacent to the first and second guide wires 70, 72 as though the third guide wire 78 were implanted in the right-hand pedicle of a vertebra (not shown) directly superior to the second vertebra 26. Accordingly, the method of FIGS. 1 through 23 may be used to secure together vertebrae on multiple levels, not just two adjacent vertebrae.

Figure 3:
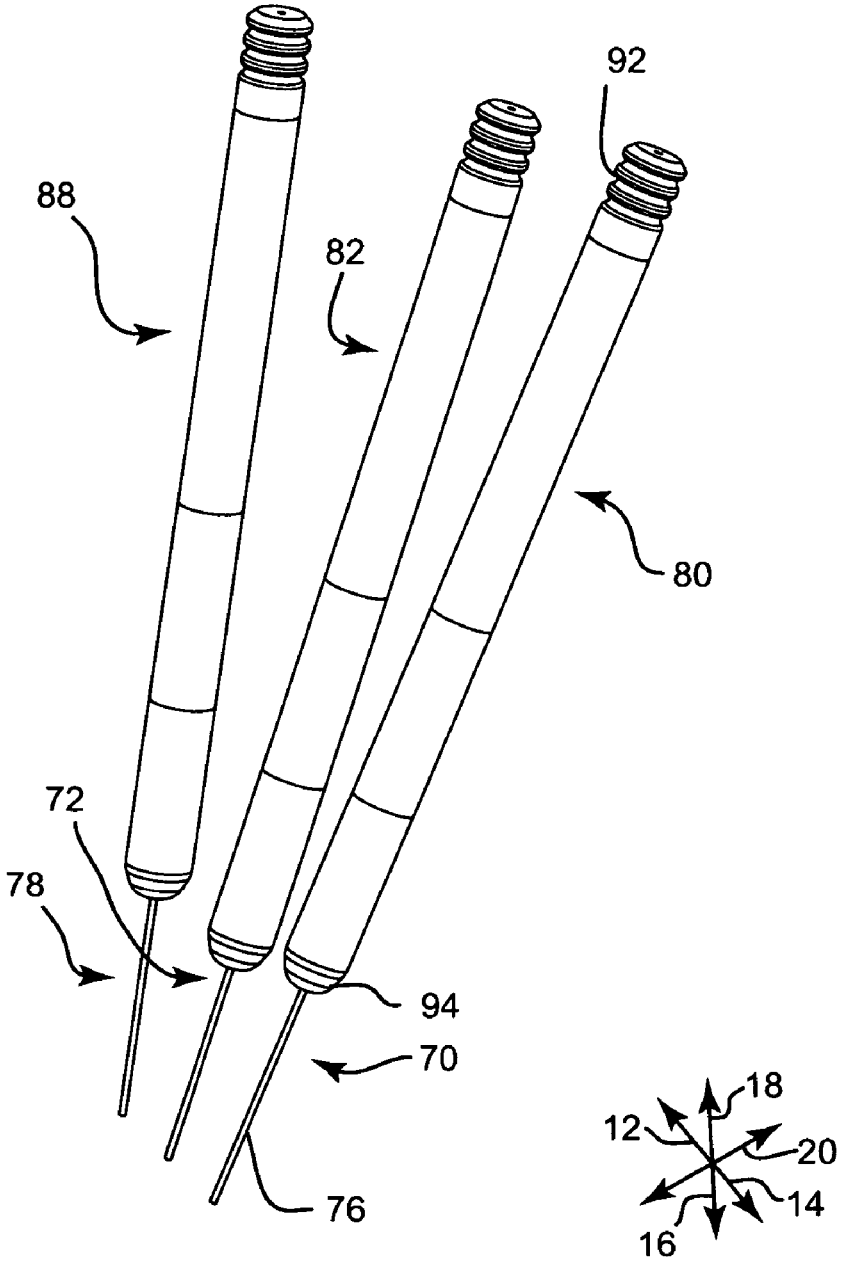
FIG. 3 is a perspective view of the guide wires of FIG. 2, with dilators advanced along the guide wires to dilate surrounding tissue.

Referring to FIG. 3, a perspective view illustrates the guide wires 70, 72, 78, in conjunction with a first dilator 80, a second dilator 82, and a third dilator 88. Each of the dilators 180, 82, 88 has a proximal end 92 and a distal end 94. The proximal ends 92 may be shaped for gripping by hand, or for attachment to a handle or the like. The distal ends 94 are rounded to permit relatively gentle spreading of tissues surrounding the guide wires 70, 72, 78 by the dilators 80, 82, 88.

Each of the dilators 80, 82, 88 has a bore sized to receive the proximal end 74 of the corresponding guide wire 70, 72, or 78, so that the dilators 80, 82, 88 are able to slide along the guide wires 70, 72, 78 toward the distal ends 74, thereby spreading the tissues away from the guide wires 70, 72, 78. Each of the dilators 80, 82, 88 may optionally include a plurality of nesting elements that permit discretely gradual dilation. As an alternative to the guide wires 70, 72, 78 and the dilators 80, 82, 88, a variety of other guiding devices and/or dilation devices may be used within the scope of the present invention.

Figure 4:
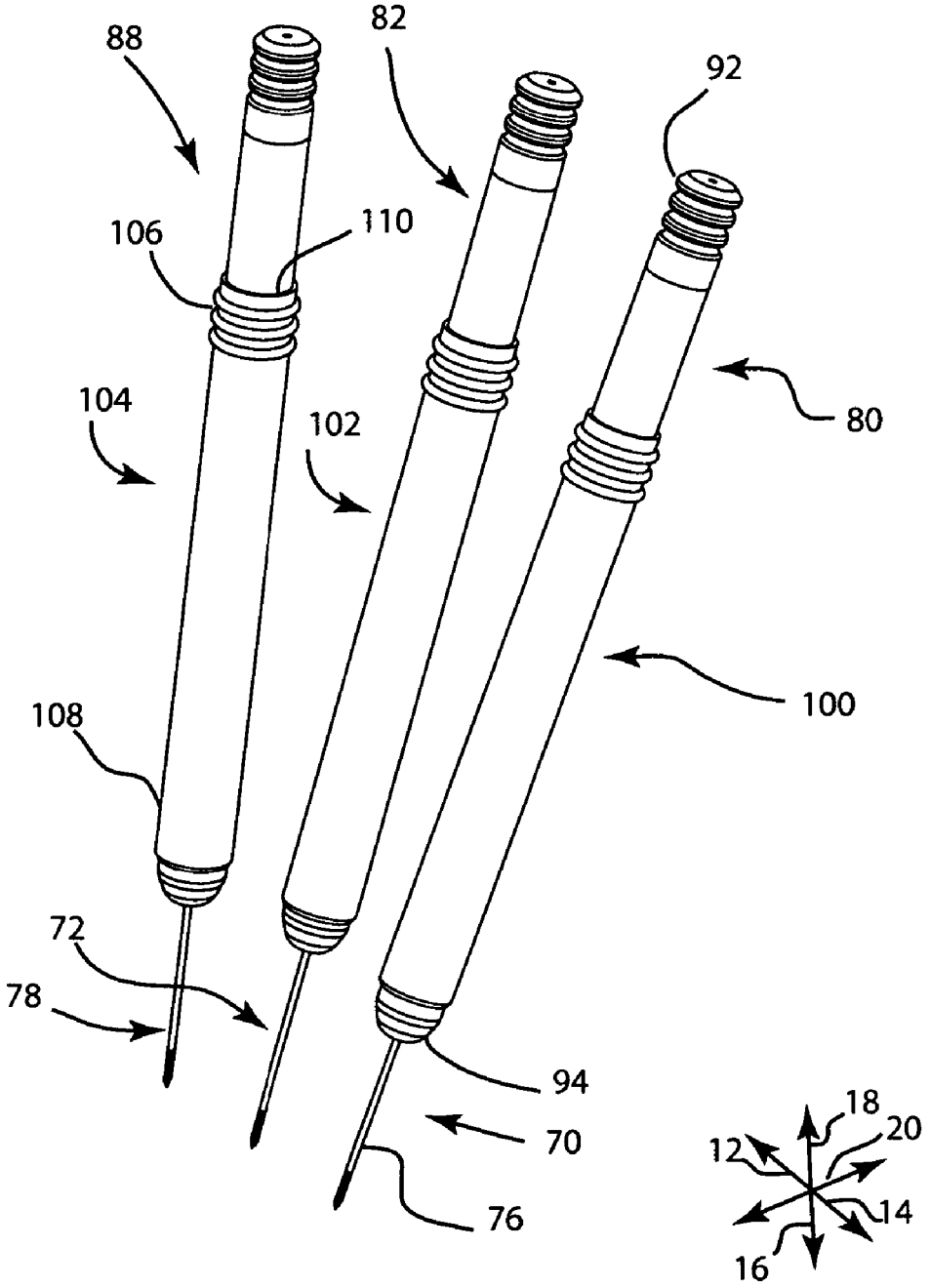
FIG. 4 is a perspective view of the guide wires and dilators of FIG. 3, with hollow dilators placed around the solid dilators.

Referring to FIG. 4, a perspective view illustrates the guide wires 70, 72, 78 and dilators 80, 82, 88 of FIG. 3, with first, second, and third hollow dilators 100, 102, 104 placed around the dilators 80, 82, 88, respectively. Each of the hollow dilators 100, 102, 104 has a generally tubular shape with a proximal end 106, a distal end 108, and a bore 110 extending from the proximal end 106 to the distal end 108. Each of the bores 110 is sized to receive the outward-facing surface of the corresponding dilator 80, 82, 88.

Accordingly, the hollow dilators 100, 102, 104 may simply slide along the anterior direction 16 between the outward-facing surfaces of the dilators 80, 82, 88 and the adjoining tissues. The hollow dilators 100, 102, 104 then reach the positions shown in FIG. 4, thereby removing the dilators 80, 82, 88 from significant contact with the tissues to be dilated.

Figure 5:
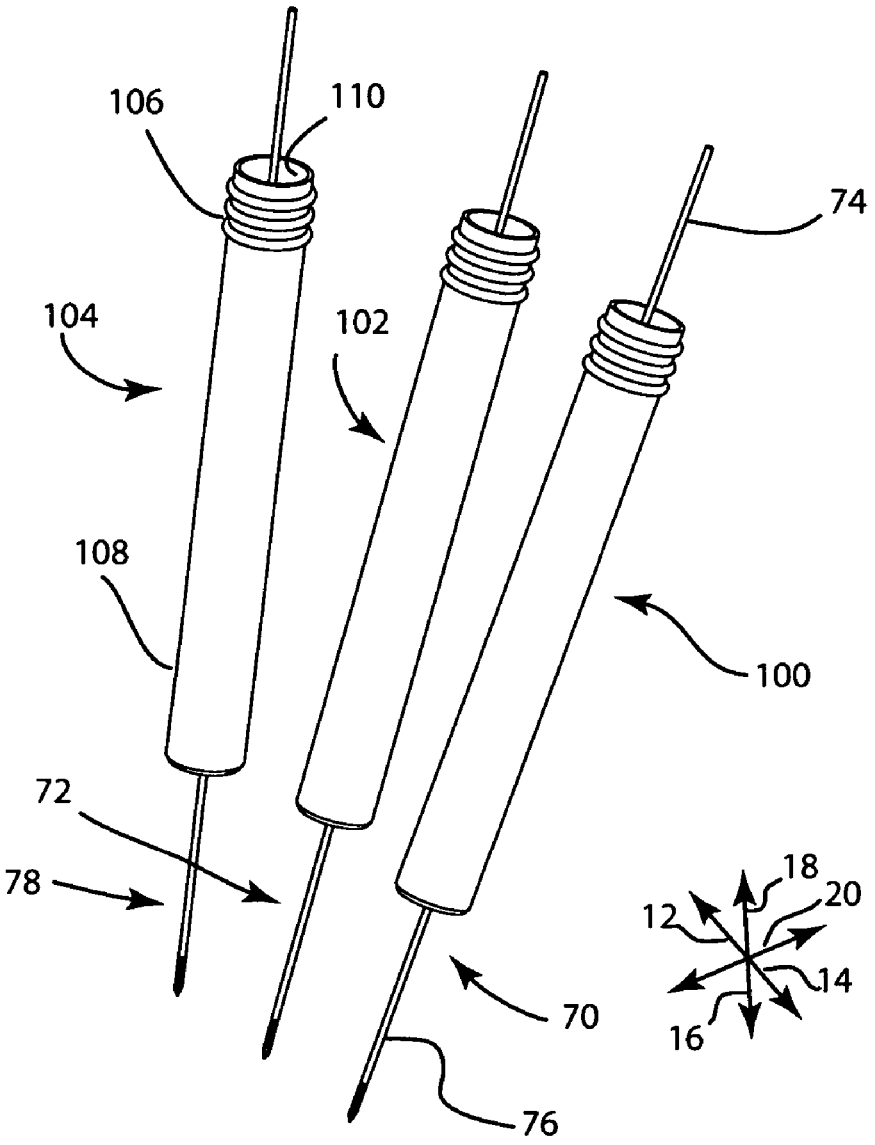
FIG. 5 is a perspective view of the guide wires and hollow dilators of FIG. 4, with the solid dilators removed.

Referring to FIG. 5, a perspective view illustrates the guide wires 70, 72, 78 and hollow dilators 100, 102, 104 of FIG. 4, with the dilators 80, 82, 88 removed. The dilators 80, 82, 88 are simply withdrawn along the posterior direction 18 from within the hollow dilators 100, 102, 104 to leave the bores 110 of the hollow dilators 100, 102, 104 unobstructed.

Figure 6:
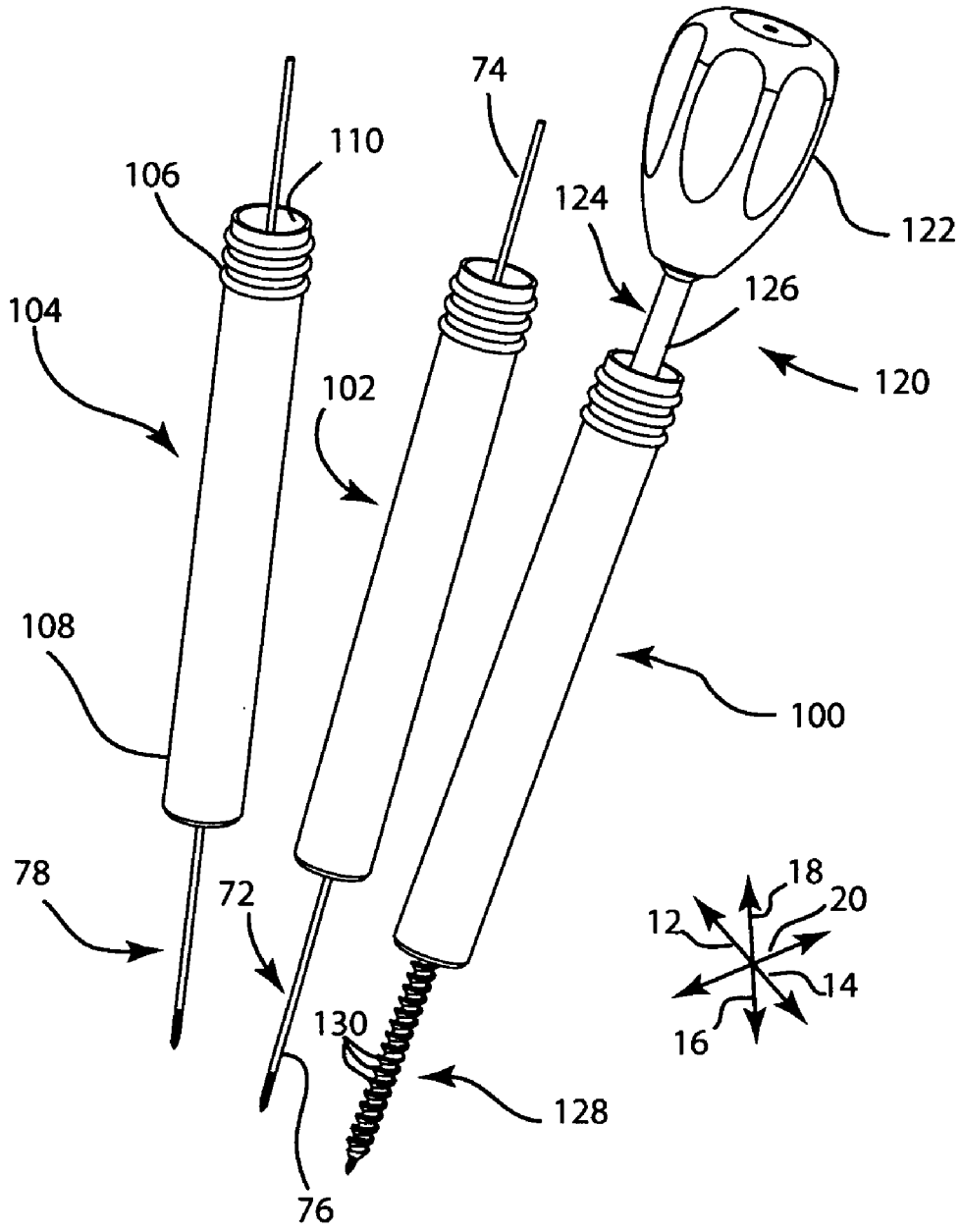
FIG. 6 is a perspective view of the guide wires and hollow dilators, with a tapping tool placed over one of the guide wires to tap the corresponding pedicle.

Referring to FIG. 6, a perspective view illustrates the guide wires 70, 72, 78 and hollow dilators 100, 102, 104, with a tapping tool 120 placed over the first guide wire 70 to tap the corresponding pedicle (not shown in FIG. 6). As shown, the tapping tool 120 may have a handle 122 shaped to be gripped by hand, and a shank 124 extending from the handle 122. The shank 124 has a proximal end 126 coupled to the handle 122 and a distal end 128 having a plurality of threads 130.

The tapping tool 120 also has a bore (not shown) extending through the shank 124 and through at least a portion of the handle 122. The bore is sized to receive any of the guide wires 70, 72, 78 so that the tapping tool 120 can be guided sequentially along each of the guide wires 70, 72, 78 to tap the pedicle 30 of the first vertebra 24, the pedicle 50 of the second vertebra 26, and the pedicle of the third vertebra (not shown in FIG. 6). Tapping is carried out by rotating the handle 122 clockwise while exerting axial pressure on the handle 122 to cause the distal end 128 to penetrate the bone. After a pedicle has been tapped, the distal end 128 is withdrawn from the tapped cavity by rotating the handle 122 counterclockwise.

Figure 7:
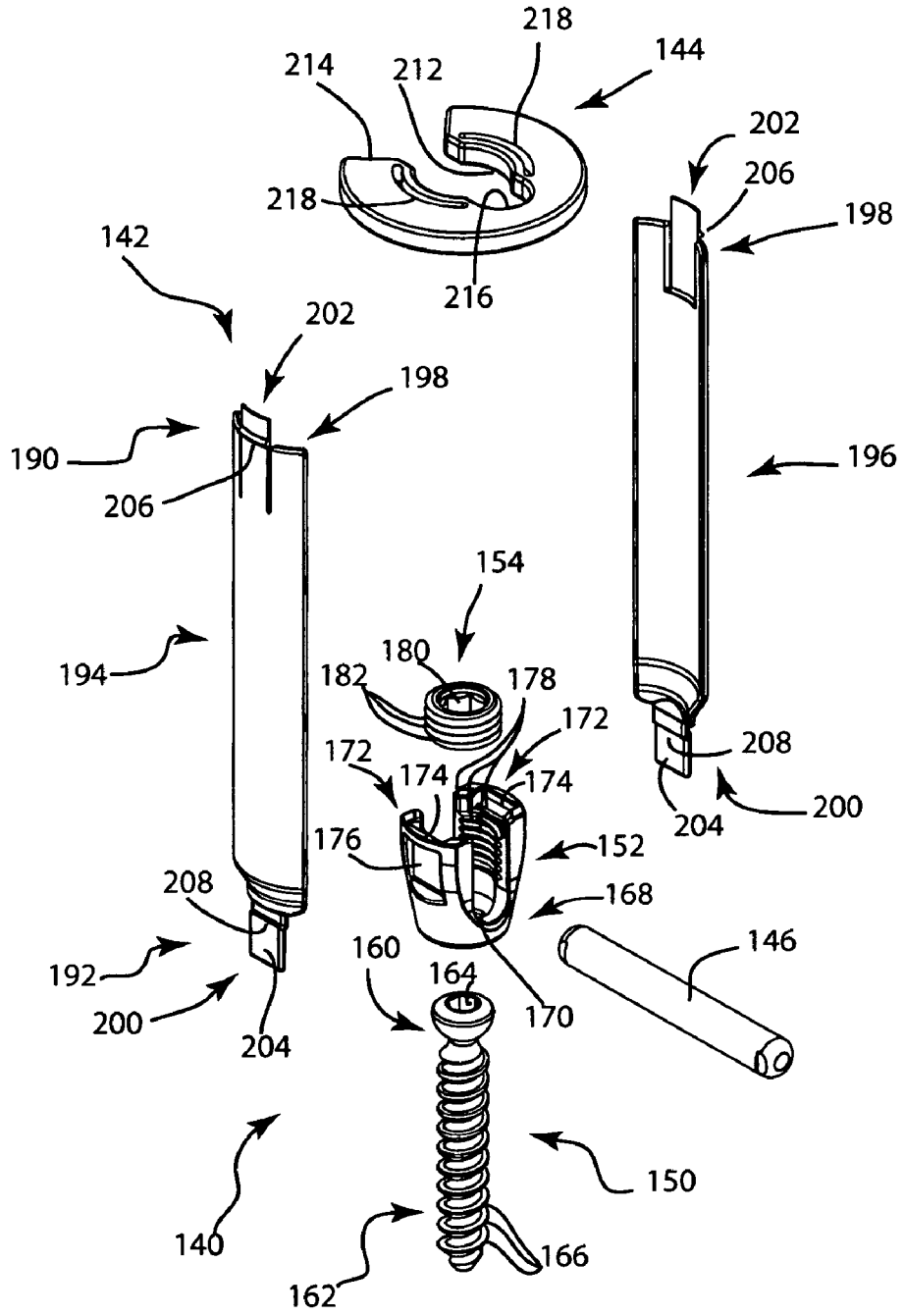
FIG. 7 is an exploded, perspective view of a cannula, abutment member, pedicle screw, cage, set screw, and a portion of a rod according to one embodiment of the invention.

Referring to FIG. 7, an exploded, perspective view illustrates a connecting element 140, a cannula 142, an abutment member 144, and a rod portion 146 according to one embodiment of the invention. The rod portion 146 is a segment of a longer rod that may be used to secure the first vertebra 24, the second vertebra 26, and the third vertebra (not shown in FIG. 7) together. The connecting element 140 is used to secure the rod portion 146 to one pedicle of the vertebrae to be secured together. The cannula 142 is used to maintain access to the connecting element 140 after it has been implanted in the pedicle in a manner that facilitates percutaneous placement of the rod portion 146 and attachment of the rod portion 146 to the connecting element 140. The abutment member 144 helps to hold the cannula 142 together and keep it secured to the connecting element 140 in a manner that will be described subsequently.

As embodied in FIG. 7, the connecting element 140 has a pedicle screw 150, a cage 152, and a set screw 154. The pedicle screw 150 is the portion of the connecting element 140 that is implanted in the corresponding pedicle. The pedicle screw 150 is able to hold the cage 152 against the pedicle at any of a variety of orientations of the cage 152 with respect to the pedicle screw 150. Thus, the cage 152 is polyaxially movable with respect to the pedicle screw 150 until the set screw 154 is tightened into the cage 152 to lock the orientation of the cage 152 with respect to the pedicle screw 150.

The pedicle screw 150 has a head 160 and a shank 162. The head 160 has a convex semispherical underside that engages the cage 152 in any of a variety of relative orientations to provide the polyaxial coupling described previously. The head 160 also has a hexagonal recess 164 designed to receive a hexagonal end of a pedicle screw driver (not shown in FIG. 7), which will be shown and described subsequently. The shank 162 has a plurality of threads 166 that rotate into threaded engagement with the tapped pedicle. The pedicle screw 150 also has a bore (not shown) extending through the shank 162 and the head 160 to receive any of the guide wires 70, 72, 78 to facilitate guiding of the pedicle screw 150 into engagement with the corresponding pedicle.

The cage 152 has a base 168 in which an aperture 170 is formed. The aperture 170 is sized such that the shank 162 of the pedicle screw 150 may be inserted through the aperture 170. The head 160 of the pedicle screw 150 then rests on a concave semispherical surface of the base 168, within which the head 160 is polyaxially rotatable. The cage 152 also has a pair of arms 172 that extend from the base 168, generally parallel to each other. Each of the arms 172 has a slot 174 and an exterior recess 176. The slots 174 pass through the arms 172 to communicate with the slots 174. Each of the arms 172 has an inward-facing surface on which a plurality of threads 178 are formed to receive the set screw 154. The arms 172 define recesses therebetween, and the recesses form ends of a trough in which the rod portion 146 is able to rest.

As shown, the set screw 154 has a hexagonal recess 180 that enables the set screw 154 to be rotated by a driver that will be shown and described subsequently. The set screw 154 also has an outward-facing surface on which a plurality of threads 182 are formed to enable the set screw 154 to rotate into threaded engagement with the cage 152. Once the rod portion 146 is positioned between the arms 172 of the cage 152, the set screw 154 may be tightened to press the rod portion 146 against the head 160 of the pedicle screw 150, thereby resisting further relative rotation between the cage 152 and the pedicle screw 150.

Upon assembly, the cannula 142, which is shown in exploded form in FIG. 7, will have a proximal end 190 and a distal end 192. The cannula 142 may be dimensioned such that the proximal end 190 protrudes above the skin, while the distal end 192 is securable to the cage 152 and is insertable through the skin along with the cage 152. The cannula 142 includes a first blade 194 and a second blade 196, which may be substantially identical to each other. Each of the blades 194, 196 has a proximal end 198 corresponding to the proximal end 190 of the cannula 142, and a distal end 200 corresponding to the distal end 192 of the cannula 142.

Each proximal end 198 has a proximal tab 202, and each distal end 200 has a distal tab 204. Each proximal tab 202 has a locking ridge 206 that protrudes generally outward, and extends generally circumferentially. Each proximal tab 202 is also elongated, with a thin cross section that permits bending toward and away from the axis (not shown) of the cannula. Each distal tab 204 has bends 208 that cause the distal tab 204 to jut outward, while remaining generally parallel with the remainder of the corresponding blade 194 or 196.

Each of the distal tabs 204 is insertable through the slot 174 of the adjacent arm 172 of the cage 152 when the corresponding blade 194 or 196 is tilted to position the proximal end 198 inward relative to the distal end 200. Once the distal tabs 204 have passed through the slots 174, rotation of the blades 194 or 196 back to a position generally parallel to each other, and to the axis of the cage 152, causes the distal tabs 204 to lie within the exterior recesses 176 of the arms 172 such that the bends 208 are unable to slide back through the slots 174. Thus, the blades 194, 196 are then in a locked configuration, and cannot be detached from the cage 152 until they are again moved to the unlocked configuration, i.e., tilted to position the proximal ends 198 inward.

As long as the blades 194, 196 remain generally parallel to each other, the distal end 192 of the cannula 142 remains secured to the cage 152. Thus, the distal tabs 204 form a docking element that removably secures the cannula 142 to the connecting element 140. The abutment member 144 serves to keep the blades 194, 196 parallel to each other to keep the cannula 142 in assembled form and to simultaneously keep the cannula 142 secured to the cage 152 by keeping the blades 194, 196 from rotating into the unlocked configuration. When the cannula 142 is secured to the cage 152, the cannula 142 is in its "docked configuration." When the cannula 142 is removed from the cage 152, the cannula 142 is in its "undocked configuration."

As shown, the abutment member 144 is generally disc-shaped with a central opening 212 and an open side 214 that provides access to the central opening 212. The abutment member 144 also has an interior recess 216 in communication with the central opening 212. Furthermore, the abutment member 144 has a pair of arcuate slots 218 that extend around opposing portions of the central opening 212 and are generally coaxial with the central opening 212. The arcuate slots 218 are sized to receive the first and second blades 194, 196 and to keep the first and second blades 194, 196 generally parallel to each other, and perpendicular to the abutment member 144. Thus, the blades 194, 196 are unable to pivot to the unlocked configuration and the cannula 142 maintains a generally tubular shape.

After the distal ends 200 of the blades 194, 196 are coupled to the cage 152, the proximal ends 198 may be inserted through the arcuate slots 218 of the abutment member 144. Each of the locking ridges 206 has a wedge-like profile. Accordingly, as the locking ridges 206 pass through the arcuate slots 218, the proximal tabs 202 are urged to bend inward. Once the locking ridges 206 move out of the arcuate slots 218, the proximal tabs 202 snap back to an undeflected orientation, and the locking ridges 206 are then positioned outboard of the arcuate slots 218 to interfere with withdrawal of the proximal tabs 202 from the arcuate slots 218. Thus, the proximal tabs 202 act as a locking mechanism that restricts withdrawal of the abutment member 144 from around the cannula 142.

After the blades 194, 196 have been inserted into the arcuate slots 218, the abutment member 144 may be positioned at any of a range of positions along the cannula 142. Thus, upon implantation of the pedicle screw 150 in the corresponding pedicle, the abutment member 144 will abut the outward-facing surface of the patient's skin through which the cannula 142 passes. The abutment member 144 helps to stabilize the cannula 142 with respect to the tissues it passes through.

Figure 8:
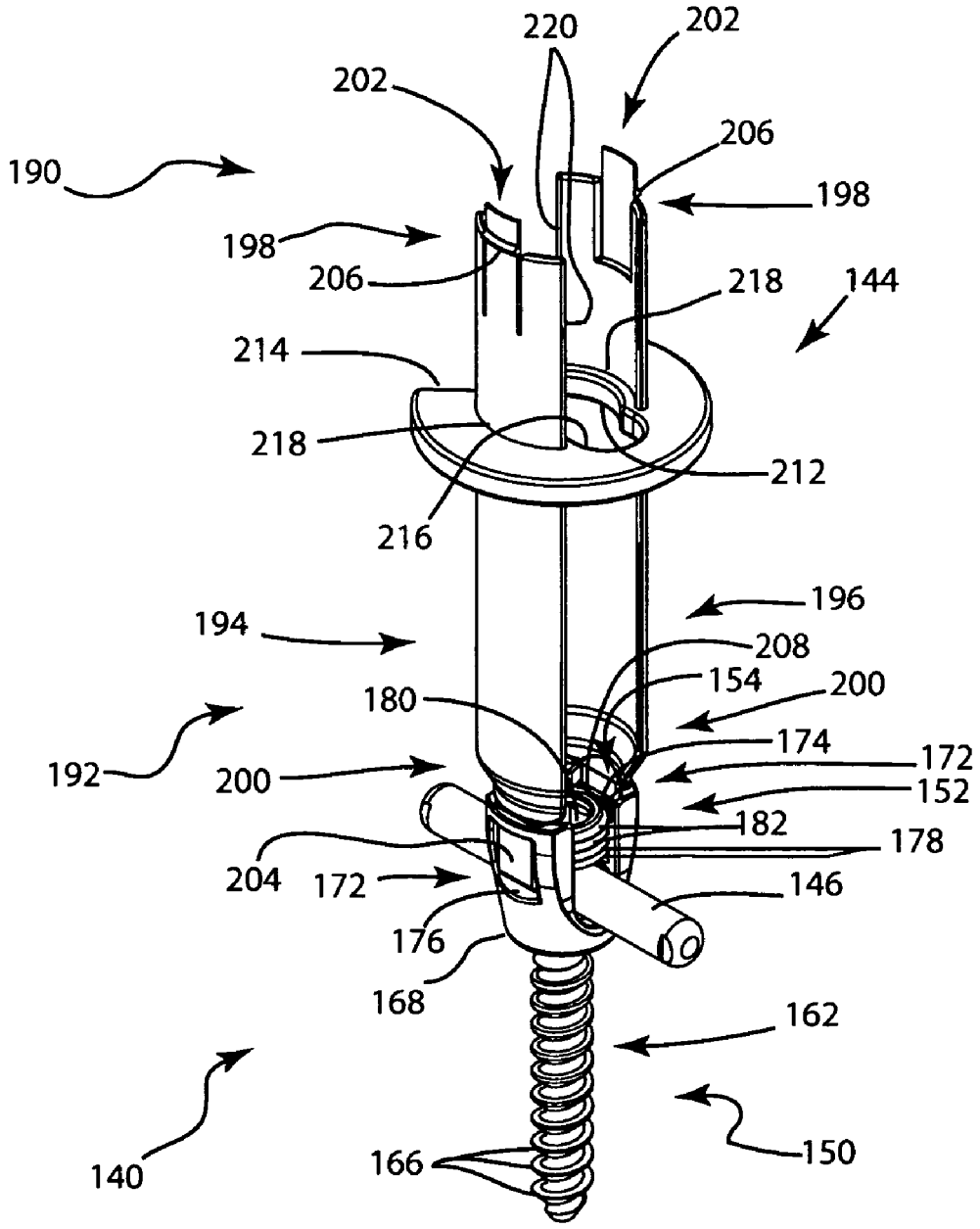
FIG. 8 is a perspective view of the cannula, abutment member, pedicle screw, cage, set screw, and rod portion of FIG. 7, in assembled form.

Referring to FIG. 8, a perspective view illustrates the connecting element 140, the cannula 142, the abutment member 144, and the rod portion 146 of FIG. 7, in assembled form. The shank 162 of the pedicle screw 150 has been inserted through the aperture 170 such that the head 160 of the pedicle screw 150 rests against the base 168 of the cage 152. The rod portion 146 has been positioned between the arms 172 and the set screw 154 has been rotated into engagement with the threads 166 of the arms 172 to keep the rod portion 146 in place and restrict further rotation of the cage 152 relative to the pedicle screw 150.

The distal tabs 204 have also been inserted through the slots 174 of the arms 172 of the cage 152, and the blades 194, 196 have been rotated into the locked configuration. The proximal ends 198 of the blades 194, 196 have been inserted through the arcuate slots 218 of the abutment member 144 to keep the blades 194, 196 in assembled form to define the cannula 142, and to keep the cannula 142 secured to the cage 152. When one or both of the blades 194, 196 are oriented in the unlocked configuration, the blades 194, 196 may still be said to define the cannula 142, although the cannula 142 then has a tapered shape.

Once assembled, the cannula 142 has slots 220 extending along its entire longitudinal length, along opposite sides of the cannula 142. The slots 220 extend to the cage 152, and are therefore contiguous with the recesses defined by the arms 172 of the cage 152. Upon implantation of the pedicle screw 150, the slots 220 will extend along the entire subcutaneous length of the cannula 142. Therefore, the rod portion 146 may be inserted percutaneously through the slots 220 along a direction transverse to the axis of the cannula 146, and may then be moved through the slots 220 along the anterior direction 16, directly into the trough of the cage 152.

Figure 9:
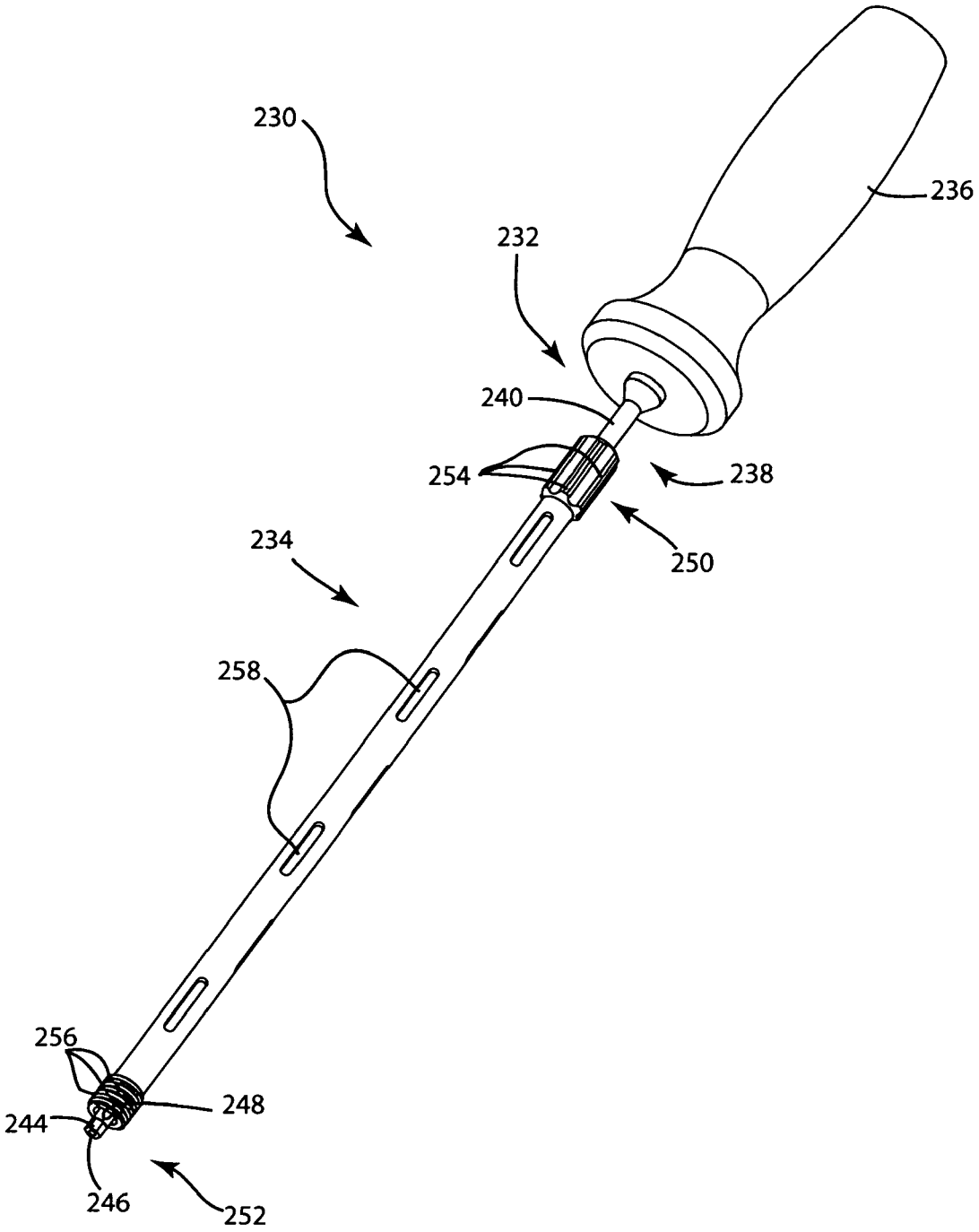
FIG. 9 is a perspective view of a screw insertion tool according to one embodiment of the invention.

Referring to FIG. 9, a perspective view illustrates a screw insertion tool 230 according to one embodiment of the invention. In the embodiment of FIG. 9, the screw insertion tool 230 has a driver 232 designed to rotate the pedicle screw 150 into threaded engagement with the corresponding tapped pedicle, and a countertorque member 234 that maintains the orientation of the cage 152 during rotation of the pedicle screw 150.

The driver 232 has a handle 236 designed to be rotated by hand, and a shank 238 extending from the handle 236. The shank 238 has a proximal end 240 and distal end 242 shaped to drive the pedicle screw 150. The distal end 242 has a hexagonal projection 244 that fits into the hexagonal recess 164 of the head 160 of the pedicle screw 150. The driver 232 also has a bore 246 sized to receive any of the guide wires 70, 72, 78; the bore 246 extends through at least a portion of the shank 238 and, optionally, through all or part of the handle 236 to permit the screw insertion tool 230 to be easily guided along each of the guide wires 70, 72, 78.

The countertorque member 234 has a bore 248 that extends along its entire length, through which the shank 238 of the driver 232 passes. The bore 248 is large enough to permit easy relative rotation between the driver 232 and the countertorque member 234. The countertorque member 234 also has a generally tubular shape with a proximal end 250 and a distal end 252. The proximal end 250 has a plurality of longitudinal ridges 254 designed to be gripped by a user's fingers to restrict rotation of the countertorque member 234. The distal end 252 has a plurality of threads 256 designed to threadably engage the threads 178 of the arms 172 of the cage 152.

Thus, the distal end 252 of the countertorque member 234 can be rotated into engagement with the cage 152 to secure the countertorque member 234 to the cage 152, thereby allowing a user to hold the longitudinal ridges 254 to keep the cage 152 stationary during rotation of the driver 232. The countertorque member 234 also has longitudinal slots 258 that provide access to the bore 248 of the countertorque member 234 for cleaning or other purposes.

Figure 10:
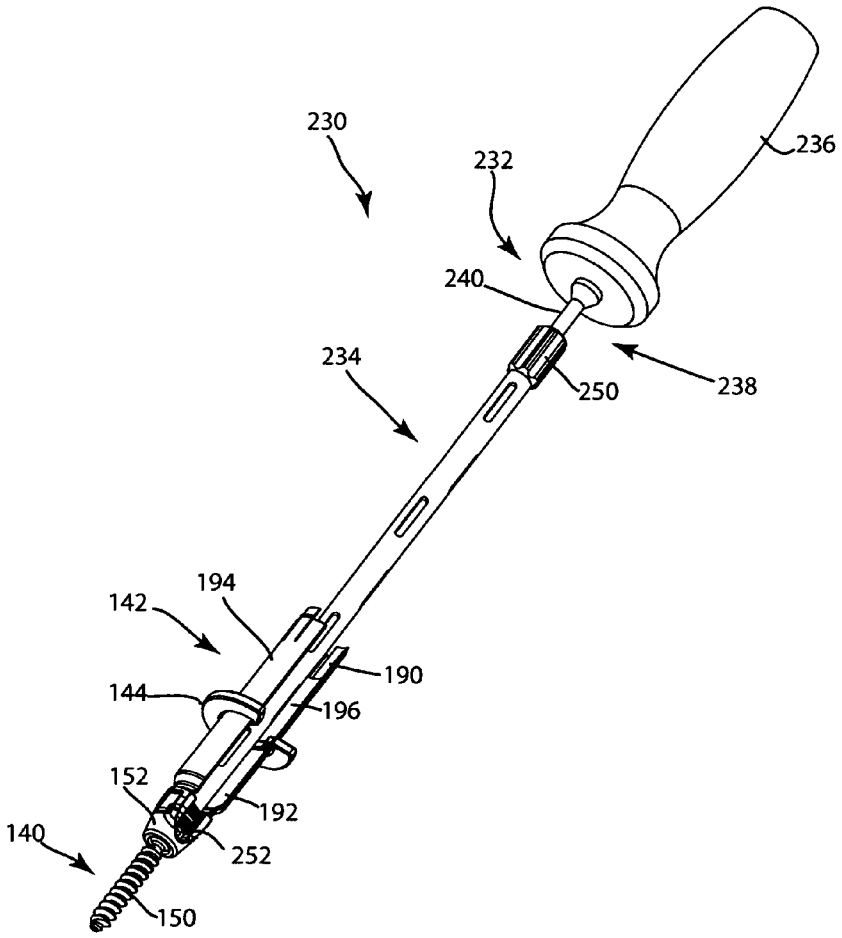
FIG. 10 is a perspective view of the screw insertion tool of FIG. 9, in engagement with the assembly of FIG. 8, excluding the rod portion and the set screw.

Referring to FIG. 10, a perspective view illustrates the screw insertion tool 230 of FIG. 9, in engagement with the assembly of FIG. 8, excluding the rod portion 146 and the set screw 154. The threads 256 of the distal end 252 have been rotated into engagement with the threads 178 of the arms 172, and the hexagonal projection 244 has been inserted into the hexagonal recess 164 of the head 160 of the pedicle screw 150. The screw insertion tool 230 is thus ready to implant the pedicle screw 150 into the corresponding tapped pedicle.

In the alternative to the embodiment illustrated in FIGS. 9 and 10, a screw insertion tool may have a countertorque member that functions independently of threaded engagement with the cage 152. For example, an alternative countertorque member (not shown) may have et projections that slide into the recesses between the arms 172, or engage other features of the cage 152, to prevent relative rotation between the cage 152 and the countertorque member.

Figure 11:
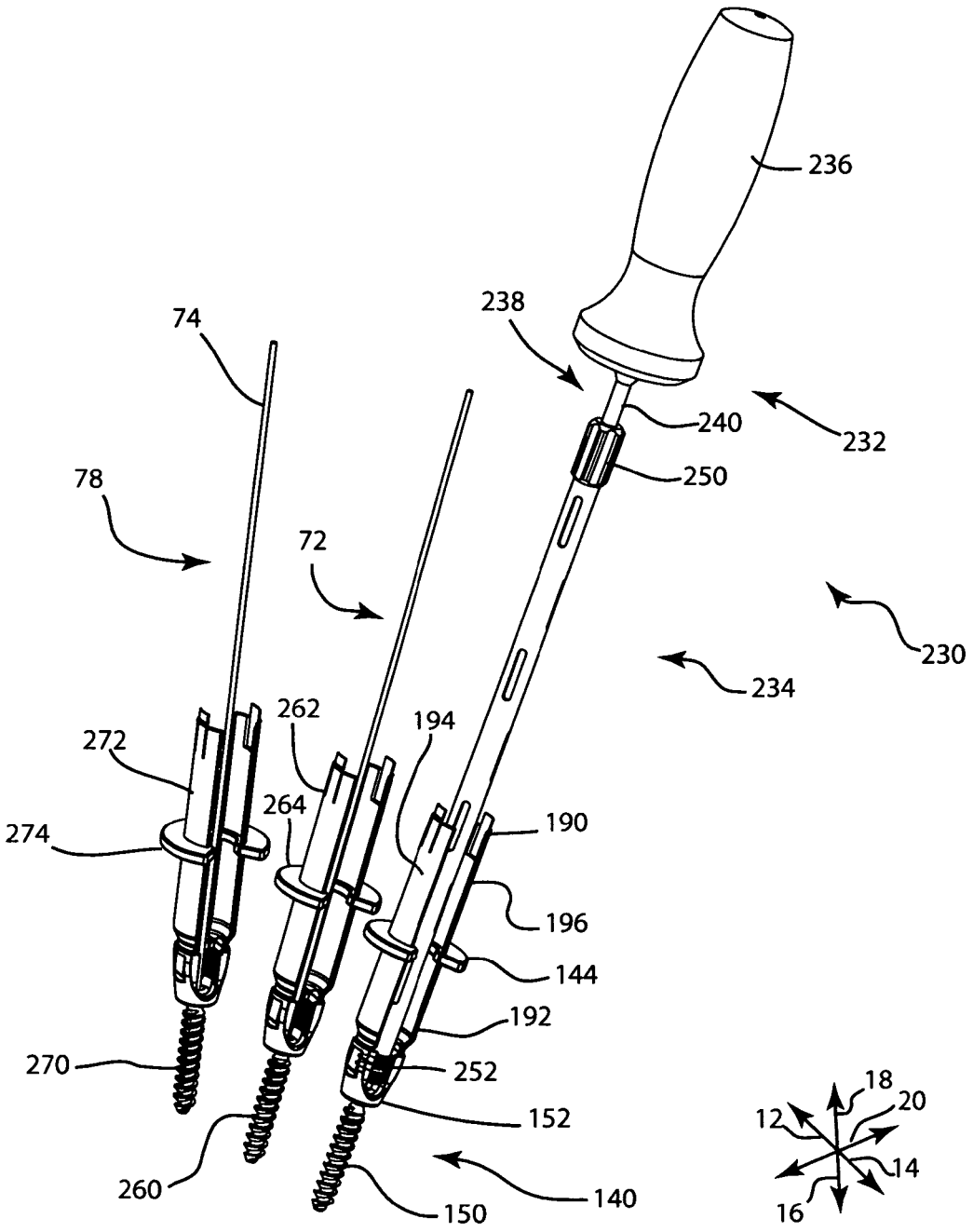
FIG. 11 is a perspective view of the screw insertion tool in use to implant the assembly of FIG. 8, excluding rod portions and set screws, over the first guide wire of FIG. 2.

Referring to FIG. 11, a perspective view illustrates the screw insertion tool 230 in use to implant the assembly of FIG. 8, excluding rod portions 146 and set screws 154, over the first guide wire 70 of FIG. 2. The handle 236 may be used to actuate the connecting element 140, the cannula 142, and the abutment member 144 along the first guide wire 70. Upon contact of the pedicle screw 150 with the tapped pedicle 30 (not shown in FIG. 11), the handle 236 is rotated while the countertorque member 234 is restrained from rotation via application of pressure on the longitudinal ridges 254. Thus, the pedicle screw 150 is rotated into engagement with the pedicle while keeping the cage 152, the cannula 142, and the abutment member 144 at a relatively constant orientation. As shown, the cannula 142 is oriented such that the slots 220 generally face in the cephalad direction 12 and the caudal direction 14.

As also shown, a second connecting element 260 has been implanted in the pedicle 50 of the second vertebra 26 (not shown in FIG. 11). A second cannula 262 and a second abutment member 264 have been secured to the second connecting element 260 in a manner similar to that of the cannula 142 and the abutment member 144. A third connecting element 270 has been implanted in the pedicle of the third vertebra (not shown in FIG. 11). A third cannula 272 and a third abutment member 274 have been secured to the third connecting element 270 in a manner similar to that of the cannula 142 and the abutment member 144. The second connecting element 260, cannula 262, and abutment member 264 and the third connecting element 270, cannula 272, and abutment member 274 may be substantially identical to the connecting element 140, the cannula 142, and the abutment member 144, as shown in FIGS. 7 and 8.

Figure 12:
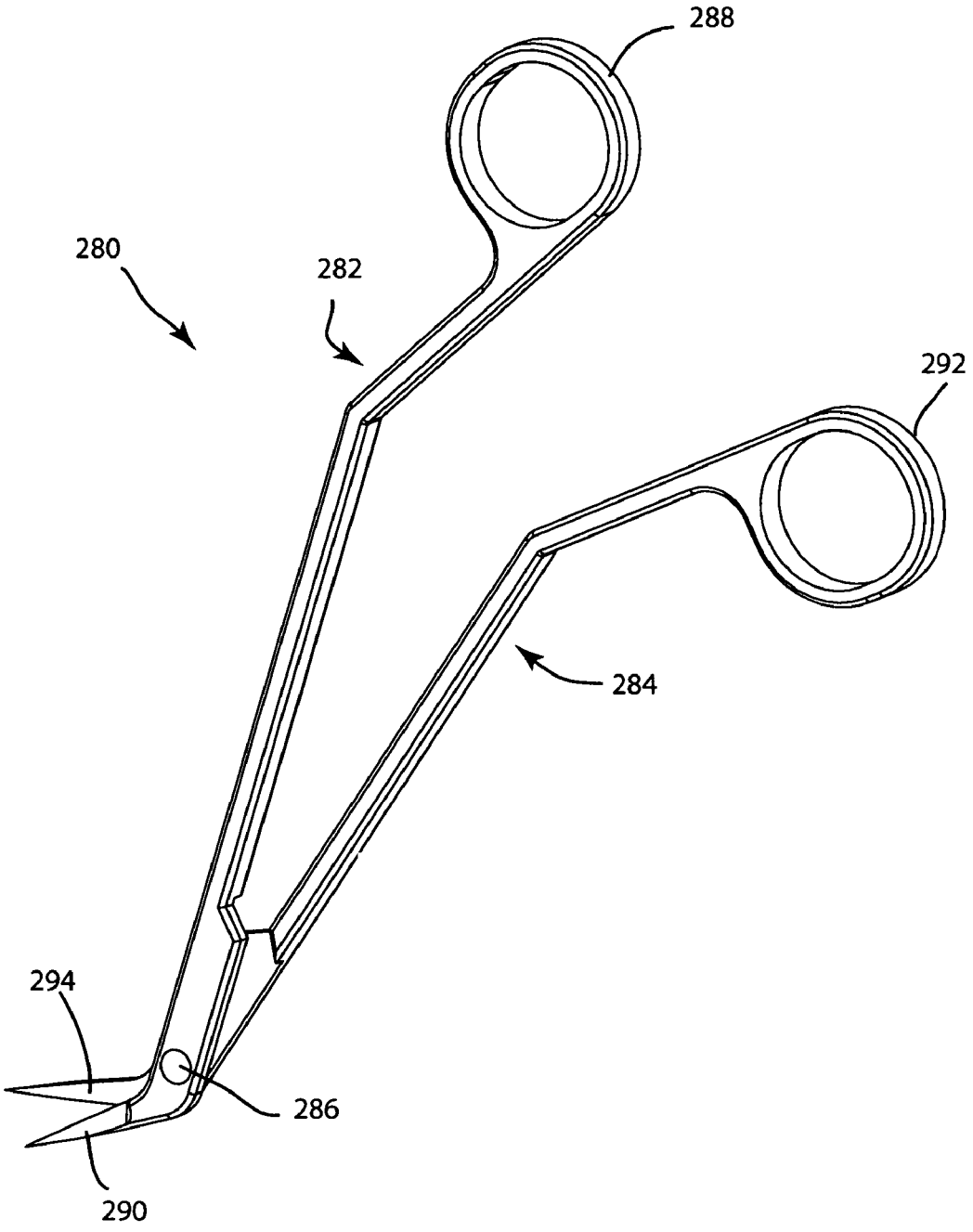
FIG. 12 is a perspective view of a fascia clipping tool according to one embodiment of the invention.

Referring to FIG. 12, a perspective view illustrates a fascia clipping tool 280 according to one embodiment of the invention. As shown, the fascia clipping tool 280 has a first member 282 and a second member 284 pivotably secured to the first member 284 through the use of a pin 286. The first member 282 has a finger loop 288 designed to receive a user's finger, and a blade 290 extending at a predefined angle from the remainder of the first member 282. Similarly, the second member 284 has a finger loop 292 and a blade 294. The blades 290, 294 have inwardly-oriented sharp edges that provide a scissoring effect when the blades 290, 294 are brought into a parallel configuration.

Figure 13:
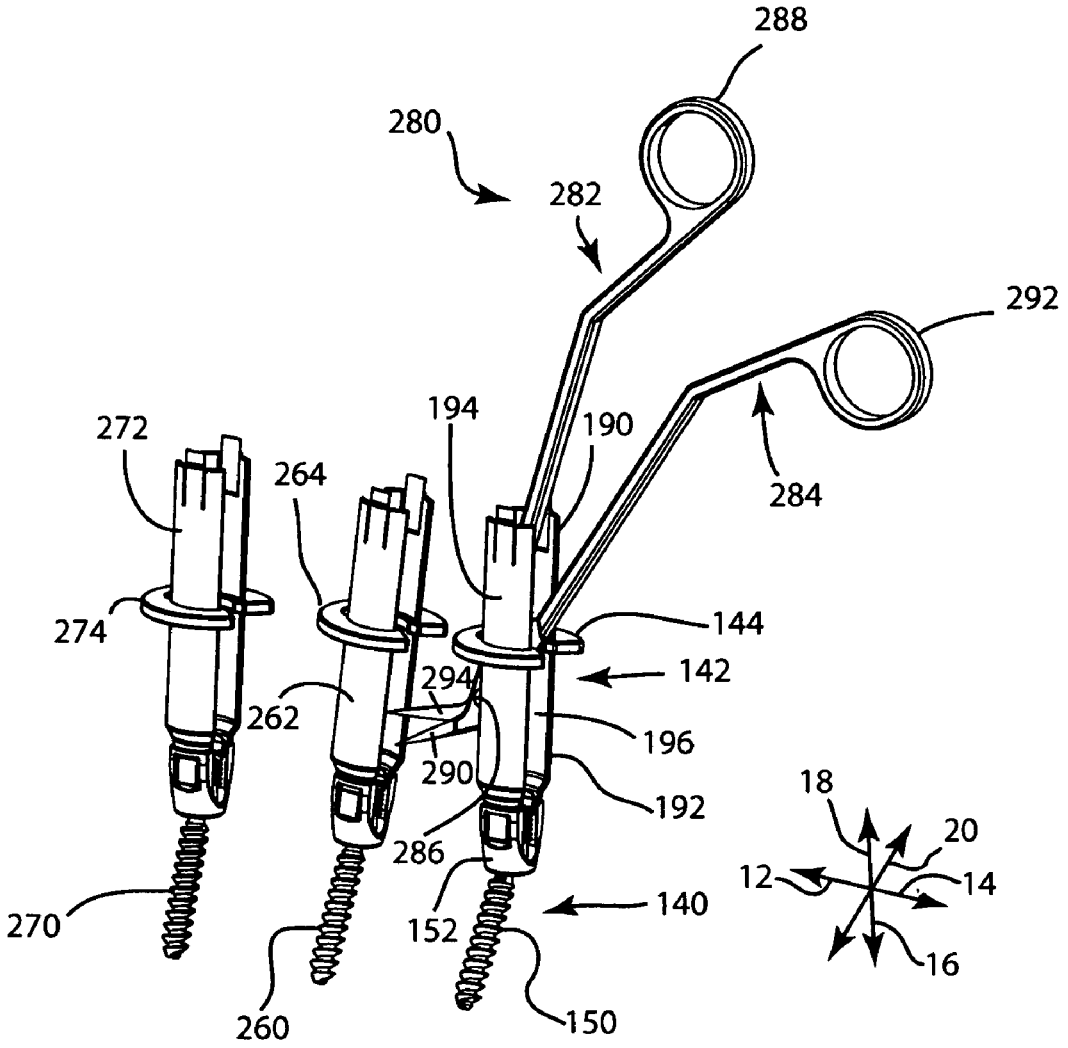
FIG. 13 is a perspective view of the fascia clipping tool of FIG. 12 inserted into one of the cannulas of FIG. 11 to sever the adjoining fascia.

Referring to FIG. 13, a perspective view illustrates the fascia clipping tool 280 of FIG. 12 inserted into the cannula 142 of FIG. 11 to sever the adjoining fascia (not shown). The skin between the cannulas 142, 262, 272 need not be severed; rather, only the subcutaneous fascia is cut to provide unimpeded percutaneous access to the cages 152 of the connecting elements 150, 260, 270. The open side 214 and the interior recess 216 of each of the abutment members 144, 264, 274 provides the appropriate range of relative motion in the cephalad and caudal directions 12, 14 for the first and second members 282, 284 to permit relatively easy cutting of the fascia with little or no damage to the surrounding tissue (not shown).

Figure 14:
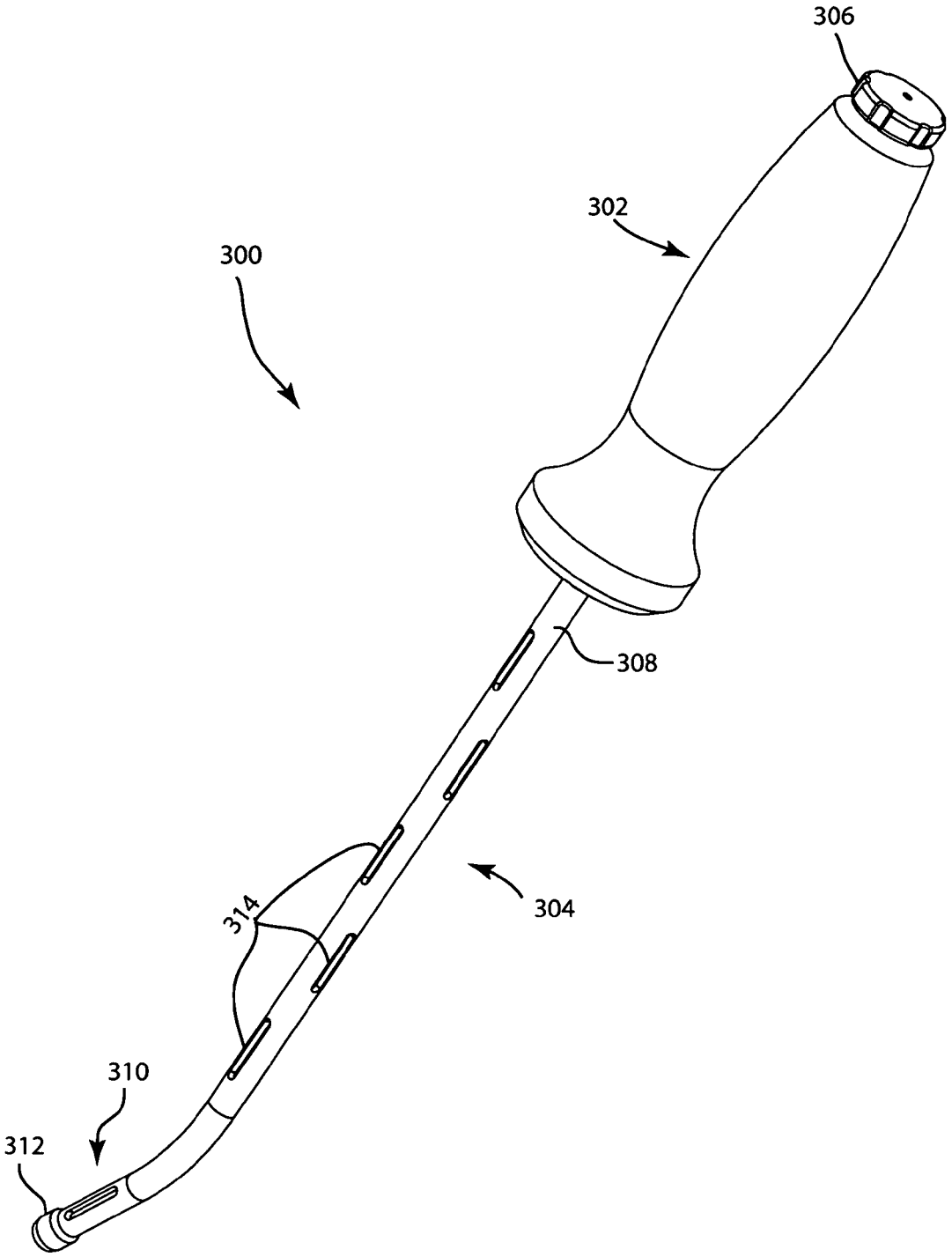
FIG. 14 is a perspective view of a rod insertion tool according to one embodiment of the invention.

Referring to FIG. 14, a perspective view illustrates a rod insertion tool 300 according to one embodiment of the invention. As shown, the rod insertion tool 300 has a handle 302 shaped to be grasped by hand, and a shank 304 extending from the handle 302. The handle 302 has a knob 306 that can be rotated by hand to control retention of a rod (not shown in FIG. 14) by the rod insertion tool 300. The shank 304 has a proximal end 308 secured to the handle 302 and a distal end 310 that receives and is securable to the end of the rod.

More precisely, the distal end 310 may have a rod coupling 312 securable to the rod through the use of a mechanism such as a collet or gripper. Such a mechanism may be actuated by rotating the knob 306. According to alternative embodiments of the invention, an interference fit or another similar mechanism may be used to retain the rod in such a manner that the rod can be removed when a threshold removal force is applied. The shank 304 has a plurality of slots 314 distributed along the length of the shank 304 to provide access to a bore (not shown) of the shank 304 for cleaning or other purposes.

Figure 15:
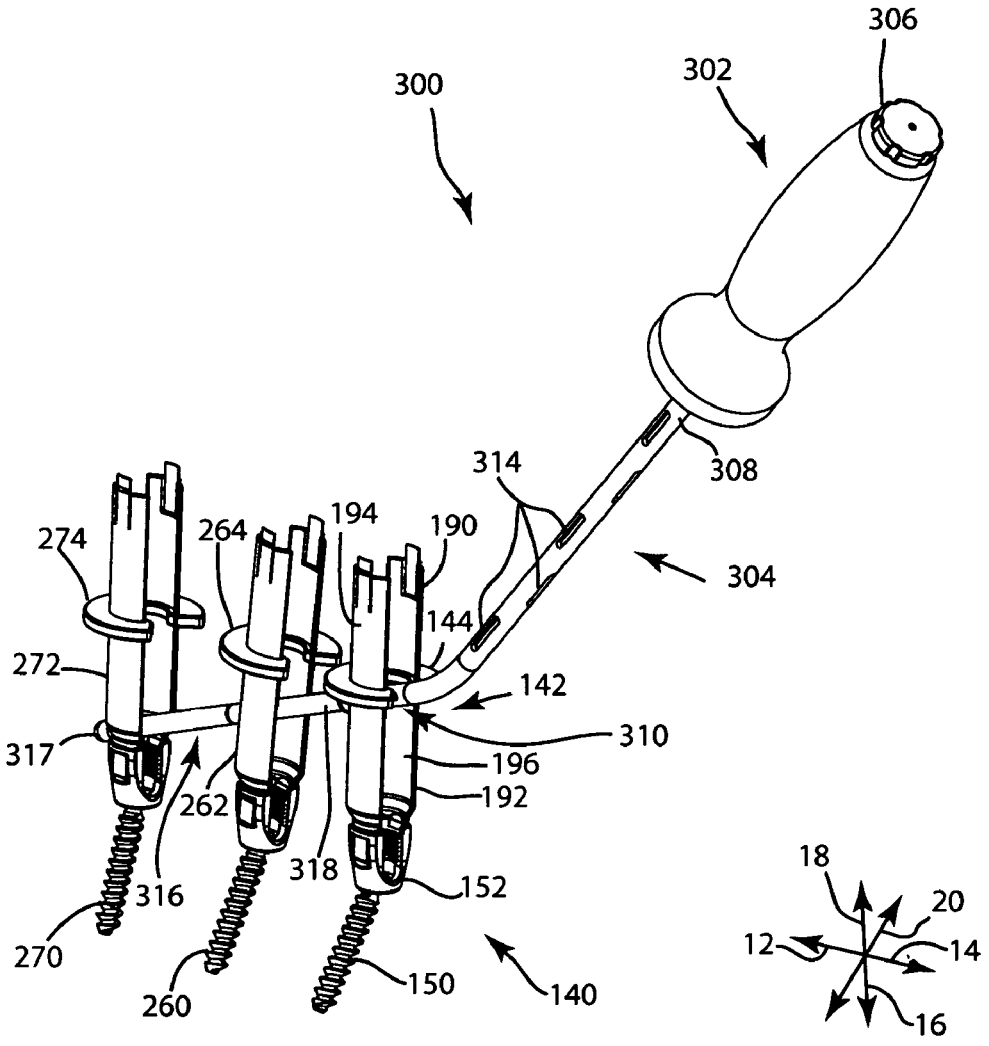
FIG. 15 is a perspective view of the rod insertion tool of FIG. 14 secured to a rod to facilitate manual insertion of the rod through the cannulas of FIG. 11.

Referring to FIG. 15, a perspective view illustrates the rod insertion tool 300 of FIG. 14 secured to a rod 316 to facilitate manual insertion of the rod 316 through the cannulas 142, 262, 272 of FIG. 11. As shown, the rod 316 has a leading end 317 and a trailing end 318 secured to the rod coupling 312 of the rod insertion tool 300. Prior to insertion underneath the skin, the rod 316 may be contoured based on the morphology of the patient's spine so that the rod 316 will maintain the proper lordotic angle between the first vertebra 24, the second vertebra 26, and the third vertebra. Alternatively, the rod 316 may be pre-lordosed to provide a lordotic angle suitable for most patients. The rod 316 may optionally be selected from a kit (not shown) containing multiple, differently angled rods.

The leading end 317 is first inserted through the skin (not shown) of the patient by inserting the leading end 317 through the proximal end 190 of the cannula 142, and through the central opening 212 of the abutment member 144. Once underneath the skin, the handle 302 is manipulated to insert the leading end 317 through the opening formed in the fascia, through the slots 220 of the second cannula 262, and through at least one slot 220 of the third cannula 272 and/or through at least one recess of the cage 152 of the third connecting element 270. Then, the rod 316 may be detached from the rod insertion tool 300.

Figure 16:
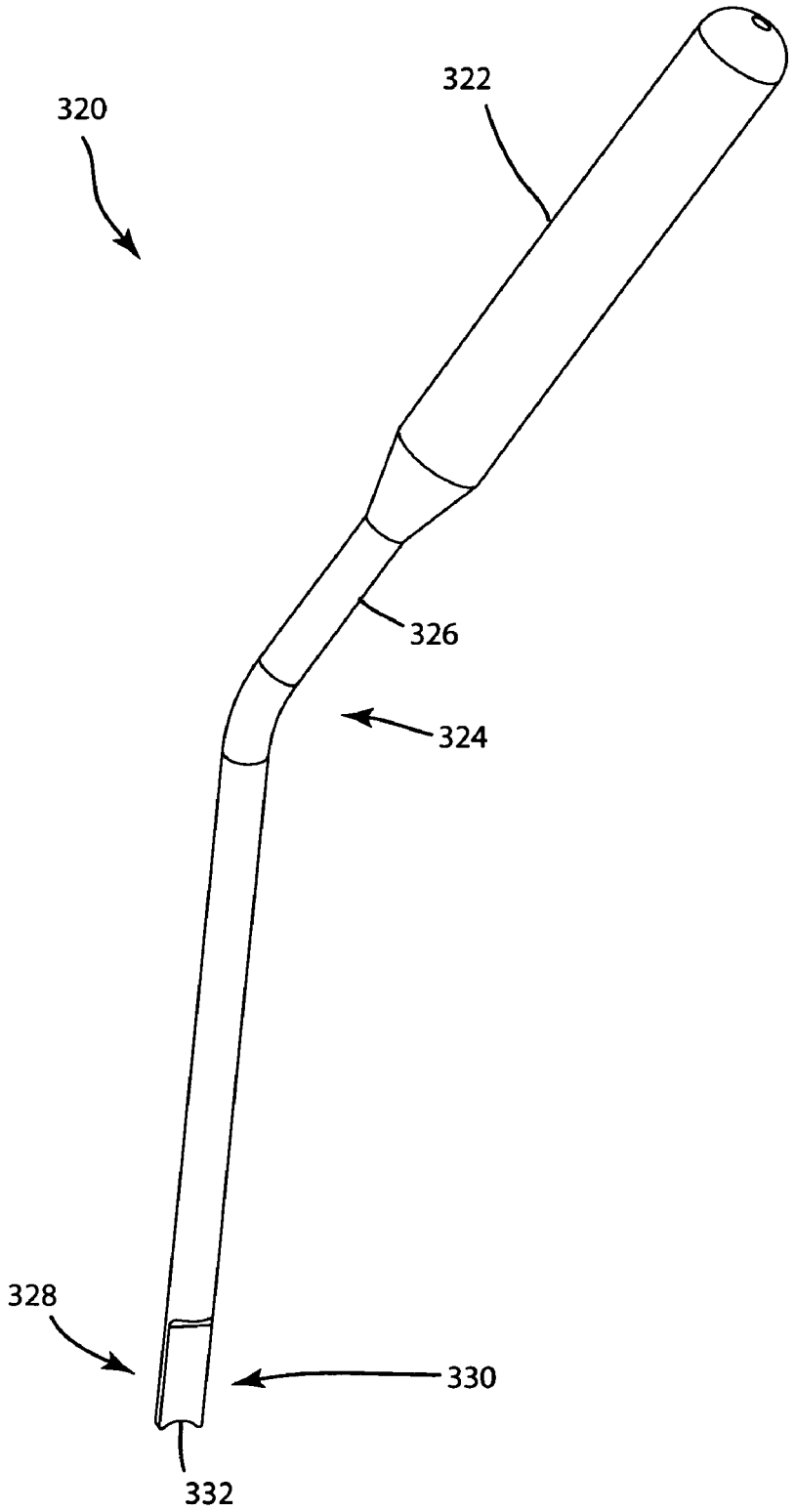
FIG. 16 is a perspective view of a rod seating tool according to one embodiment of the invention.

Referring to FIG. 16, a perspective view illustrates a rod seating tool 320 according to one embodiment of the invention. As shown, the rod seating tool 320 has a handle 322 shaped to be gripped by hand, and a shank 324 extending from the handle 322. The shank 324 has a proximal end 326 adjacent to the handle 322 and a distal end 328 shaped to push the rod 316 into place. More precisely, the distal end 328 may have a blade 330 with a generally thin cross section. The blade 330 may terminate in an arcuate recess 332 with a radius matching that of the rod 316.

Figure 17:
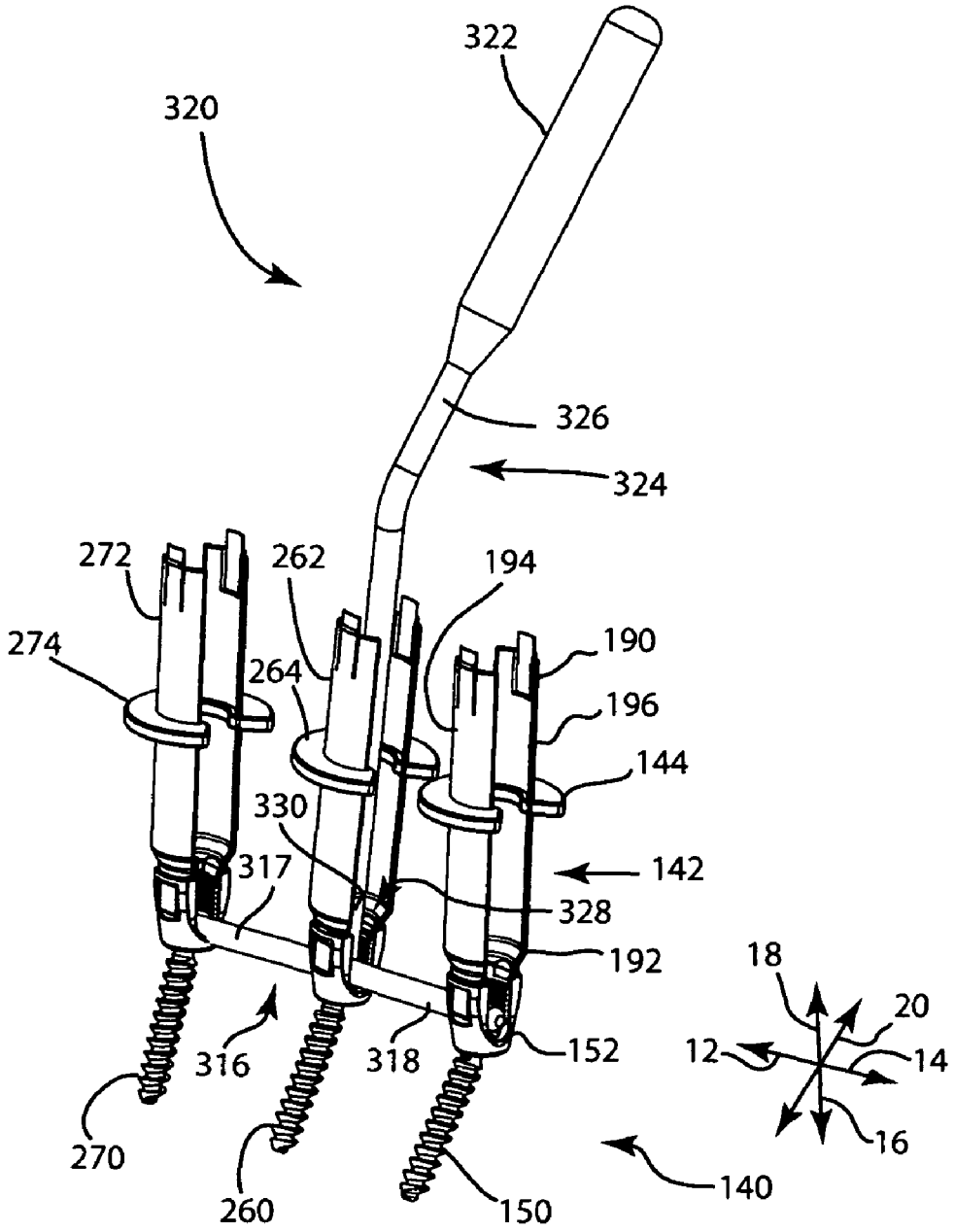
FIG. 17 is a perspective view of the rod seating tool of FIG. 16 inserted into one of the cannulas of FIG. 11 to help seat the rod in the cages.

Referring to FIG. 17, a perspective view illustrates the rod seating tool 320 of FIG. 16 inserted into the second cannula 262 of FIG. 11 to help seat the rod 316 in the cages 152 of the connecting elements 140, 260, 270. As shown, the distal end 328 of the rod seating tool 320 may simply be inserted through the second cannula 262 until the arcuate recess 332 of the blade 330 abuts the rod 316. Then, pressure is applied via the handle 322 to urge the rod 316 to slide along the slots 220, in the anterior direction 16 until the rod 316 is seated generally within the troughs of the cages 152 of the connecting elements 140, 260, 270. The distal end 328 may similarly be inserted into the cannula 142, the third cannula 272, or any combination of the cannulas 142, 262, 272 until the rod 316 has been positioned to pass through all of the cages 152.

Figure 18:
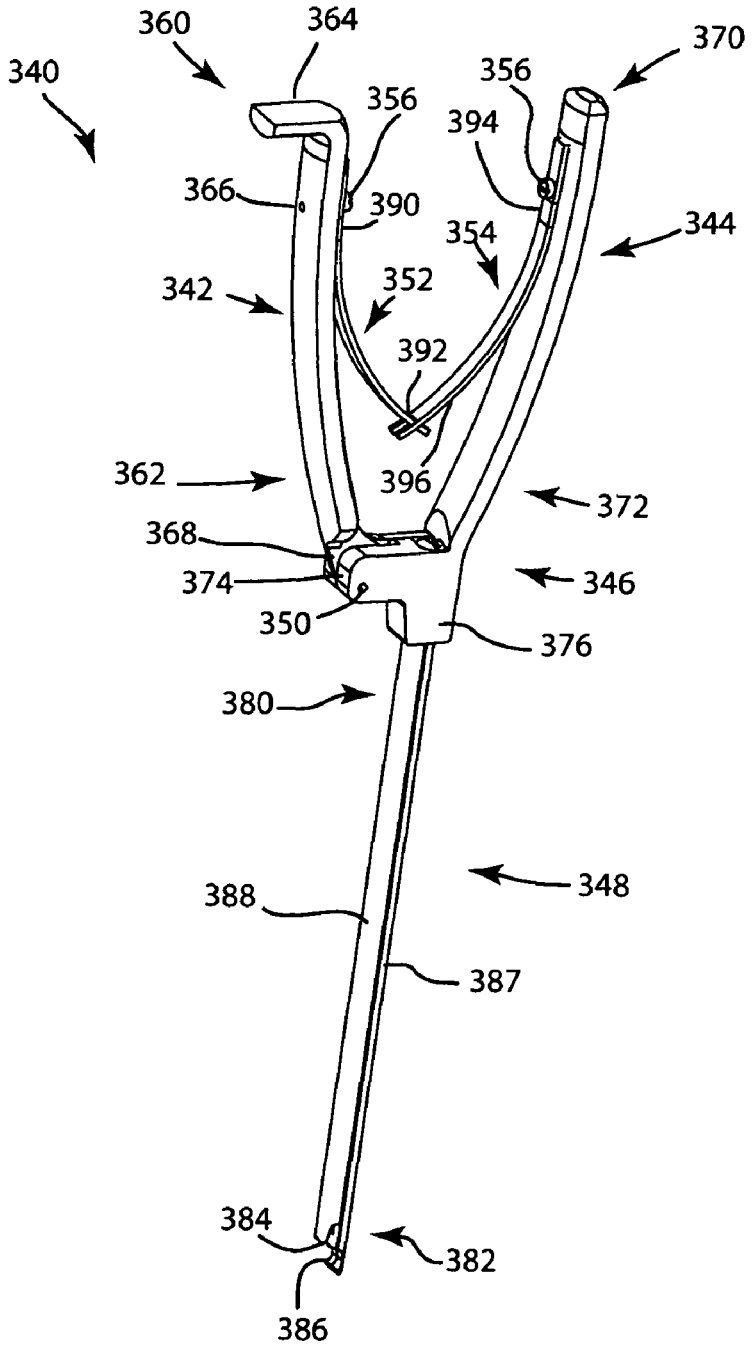
FIG. 18 is a perspective view of a rod holding tool according to one embodiment of the invention.

Referring to FIG. 18, a perspective view illustrates a rod holding tool 18 according to one embodiment of the invention. The rod holding tool 18 is designed to grip the rod 316 to permit translation of the rod 316 along its axis or rotation of the rod 316 about its axis. As embodied in FIG. 18, the rod holding tool 18 has first handle 342, a second handle 344, a central body 346, a shank 348, a pin 350, a first leaf spring 352, a second leaf spring 354, and a pair of screws 356.

The first handle 342 has a proximal end 360 and a distal end 362. The proximal end 360 has a transverse extension 364 that facilitates gripping of the first handle 342, for example, with the fingers of one hand. The proximal end 360 also has a hole 366 with threads designed to receive threads (not shown) of the corresponding screw 356. The distal end 362 has a blade 368 that is pivotably coupled to the central body 346 by the pin 350.

The second handle 344 has a proximal end 370 and a distal end 372. The proximal end 370 has a hole (not shown) similar to the hole 366 of the proximal end 360 of the first handle 342. The distal end 372 may be formed as a single piece with the central body 346. The central body 346 has a slot 374 that receives the blade 368 of the distal end 362 of the first handle 342. The pin 350 passes through the slot 374 to extend through the blade 368, thereby providing the pivotable coupling between the central body 346 and the first handle 342. The central body 346 also has a projection 376 that extends generally distally.

The shank 348 has a proximal end 380 at which the shank 348 is secured to the projection 376 of the central body 346, and a distal end 382 designed to grip the rod 316 in response to pressure applied to squeeze the first and second handles 342, 344 together. More precisely, the distal end 382 has an arcuate recess 384 with a radius matched to that of the rod 316, and an arcuate extension 386 with a radius equal or similar to that of the arcuate recess 384.

The shank 348 also has a stationary arm 387 and a sliding arm 388, each of which has a generally half-circular cross sectional shape. The stationary arm 387 is rigidly attached to the projection 376, and the sliding arm 388 is slidably coupled to the stationary arm 387. The arcuate extension 386 is on the stationary arm 387, and the arcuate recess 384 is on the sliding arm 388. The sliding arm 388 is coupled to the blade 368 of the first handle 342 within the central body 346 such that pivotal motion of the first handle 342 urges the sliding arm 388 to slide distally along the stationary arm 387.

The first leaf spring 352 has a fixed end 390 secured to the first handle 342 by the corresponding screw 356, and a coupled end 392 coupled to the second leaf spring 354. Similarly, the second leaf spring 354 has a fixed end 394 secured to the second handle 344 by the other screw 356, and a coupled end 396 coupled to the coupled end 392 of the first leaf spring 352. The coupled ends 392, 396 may be interlocked in an interdigitated manner that permits relative rotation of the coupled ends 392, 396. Thus, the leaf springs 352, 354 cooperate to provide resilient force urging the first and second handles 342, 344 to move apart, thereby urging the distal end 382 of the shank 348 to release the rod 316 in the absence of force urging the handles 342, 344 together.

In order to use the rod holding tool 340, a portion of the rod 316 may first be positioned to abut the arcuate surface of the arcuate extension 386. When the first and second handles 342, 344 are squeezed together, for example, by hand, the sliding arm 388 slides distally along the stationary arm 387. As the sliding arm 388 slides along the stationary arm 387, the arcuate recess 384 moves toward the arcuate extension 386 until the arcuate surface of the arcuate recess 384 is contiguous with the arcuate surface of the arcuate extension 386. The arcuate recess 384 then cooperates with the arcuate extension 386 to capture the rod 316 so that the rod holding tool 340 can be used to axially rotate or translate the rod 316, as desired.

Figure 19:
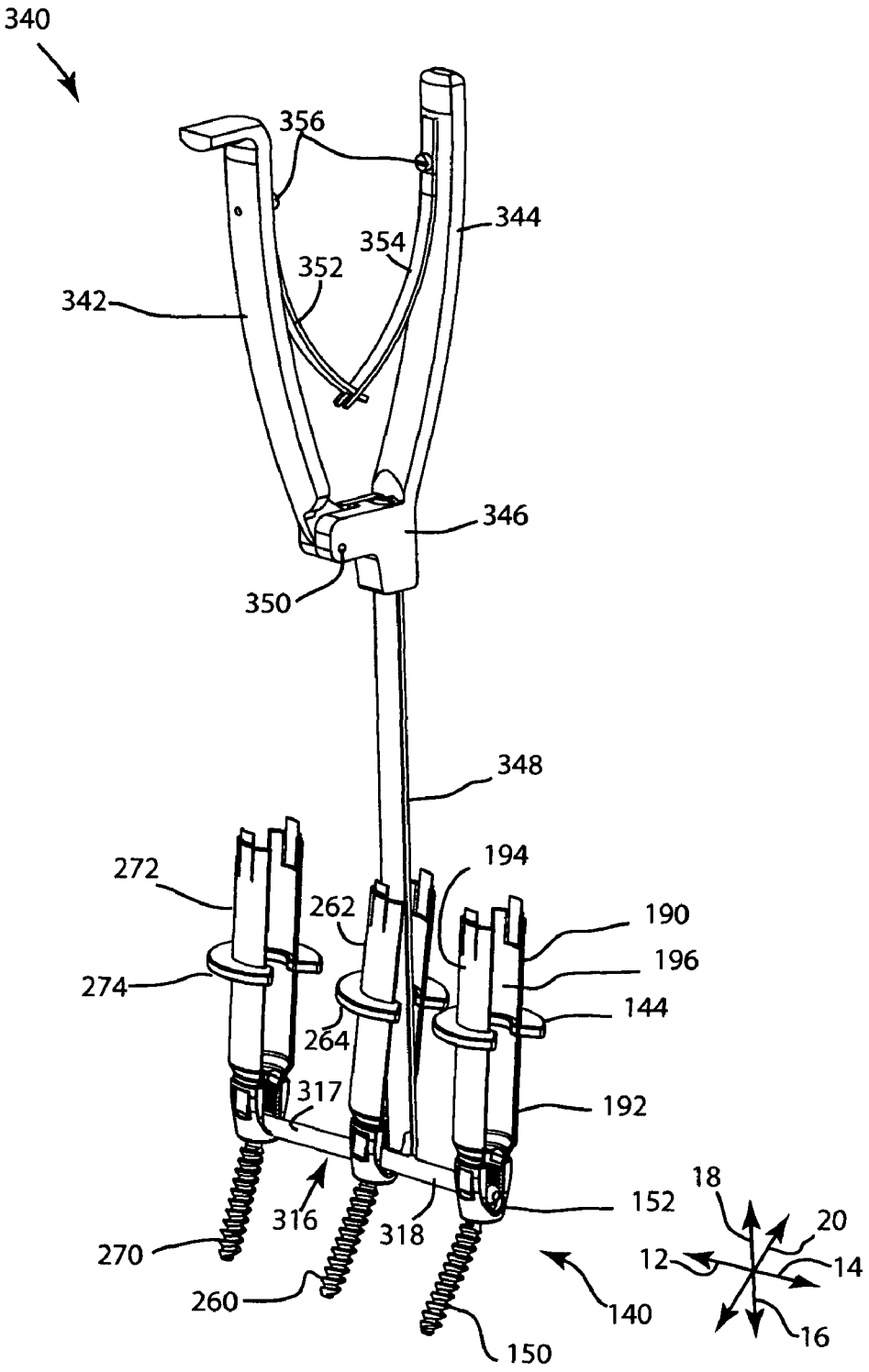
FIG. 19 is a perspective view of the rod holding tool of FIG. 18 inserted into one of the cannulas of FIG. 11 to further manipulate the rod.

Referring to FIG. 19, a perspective view illustrates the rod holding tool 340 of FIG. 18 inserted into the second cannula 262 of FIG. 11 to further manipulate the rod 316. As shown, the distal end 382 of the shank 348 has been inserted through the second cannula 262 to position the arcuate extension 386 adjacent to the rod 316. The first and second handles 342, 344 have also been squeezed together to slide the arcuate recess 384 against the rod 316 to capture the rod 316. Thus, the rod 316 can be translated or rotated in any direction. More particularly, if the rod 316 is not yet rotated to the proper orientation to pass properly through the cages 152, the rod 316 may be rotated axially through the use of the rod holding tool 340. The rod 316 may also be translated axially if needed. Fluoroscopy or other known methods may be used to check the position and orientation of the rod 316 with respect to the cages 152.

Figure 20:
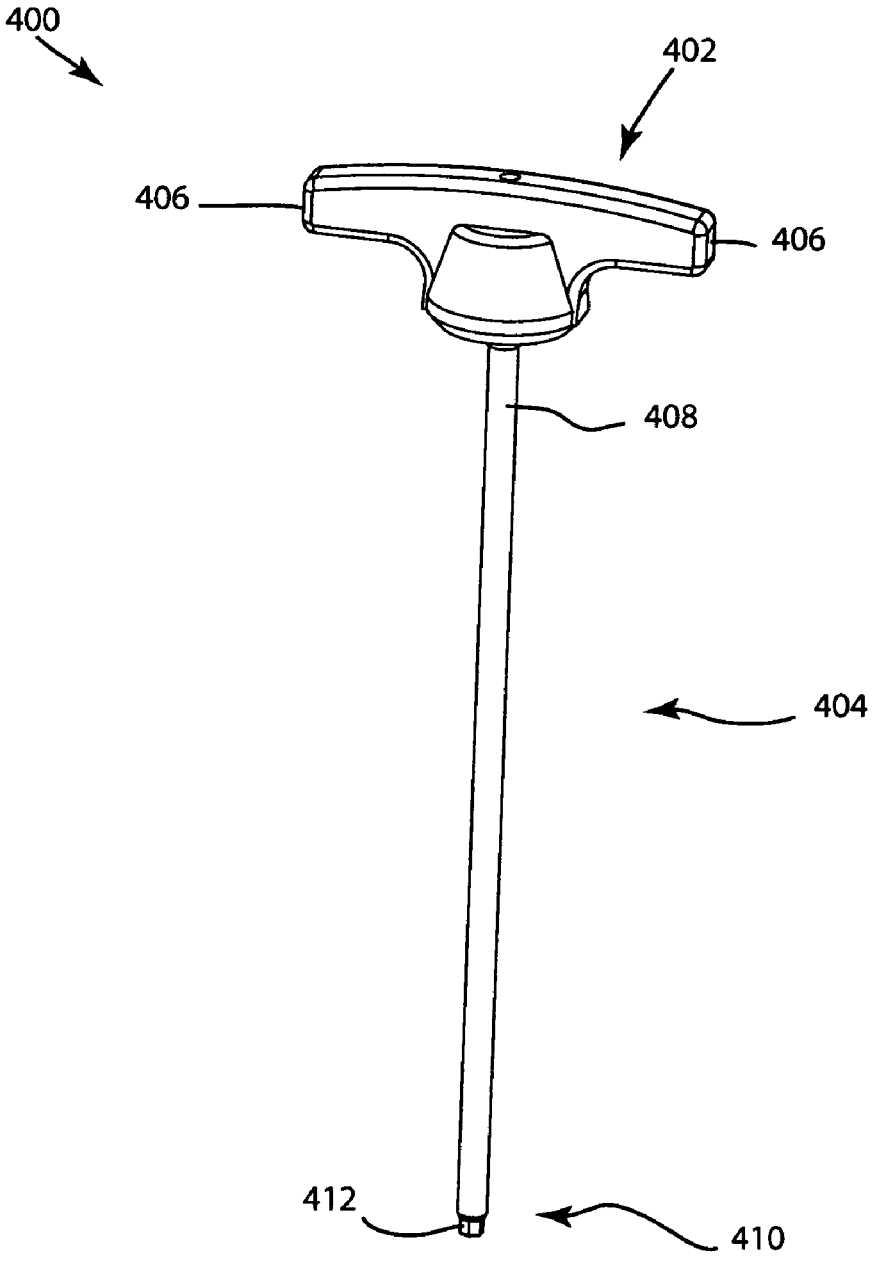
FIG. 20 is a perspective view of a set screw driver according to one embodiment of the invention.

Referring to FIG. 20, a perspective view illustrates a set screw driver 400 according to one embodiment of the invention. As shown in FIG. 20, the set screw driver 400 has a handle 402 and a shank 404 extending from the handle 402. The handle 402 has a pair of oppositely disposed transverse extensions 406 that protrude to facilitate manual gripping and rotation of the handle 402. The shank 404 has a proximal end 408 adjacent to the handle 402 and a distal end 410 designed to transmit torque to the set screw 154. The distal end 410 may have a hexagonal projection 412 insertable into the hexagonal recess 180 of the set screw 154.

Figure 21:
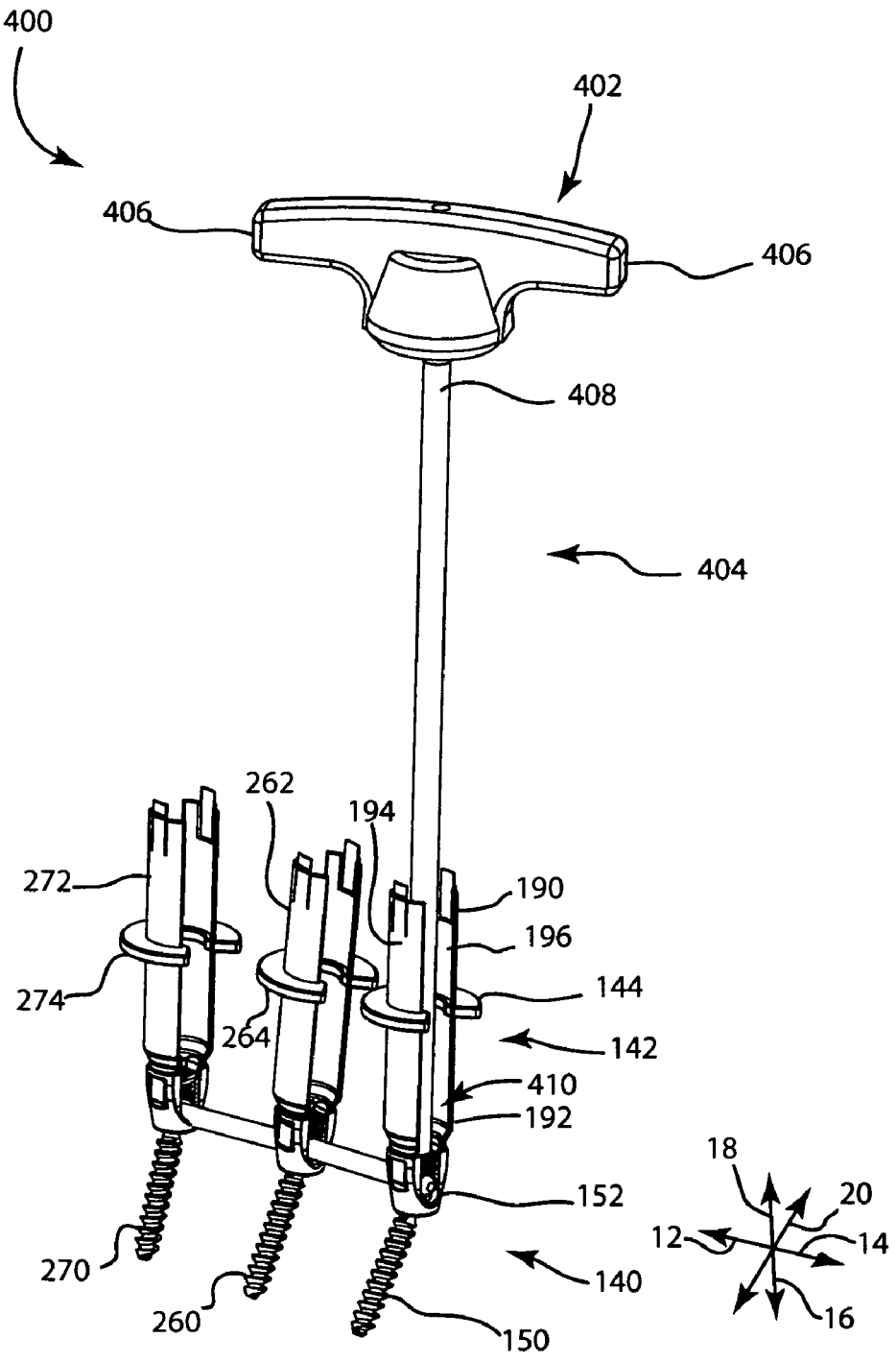
FIG. 21 is a perspective view of the set screw driver of FIG. 20 inserted into one of the cannulas of FIG. 11 to tighten a set screw to retain the rod within the corresponding cage.

Referring to FIG. 21, a perspective view illustrates the set screw driver 400 of FIG. 20 inserted into the cannula 142 of FIG. 11 to tighten the corresponding set screw 154 to retain the rod 316 within the corresponding cage 152. The set screws 154 may be applied after the rod 316 has been properly positioned with respect to the cages 152.

The hexagonal projection 412 may first be inserted into the hexagonal recess 180 of the set screw 154. Then, the handle 402 may be gripped and used to insert the set screw 154 into position adjacent to the threads 178 of the arms 172 of the cage 152 of the connecting element 140. The handle 402 may then be rotated clockwise to cause the threads 182 of the set screw 154 to rotate into engagement with the threads 178. The handle 402 may be rotated clockwise until the set screw 154 presses firmly against the rod 316 to keep the rod 316 in place within the corresponding cage 152, and to restrict further rotation of the cage 152 with respect to the corresponding pedicle screw 150. All three of the set screws 154 may be positioned and tightened in this manner to complete assembly of the posterior spinal fusion system.

In addition to the set screw driver 400 of FIGS. 20 and 21, a countertorque member (not shown) may be provided. Such a countertorque member may engage the cage 152 to keep the cage 152 from rotating while the set screw 154 is tightened.

Figure 22:
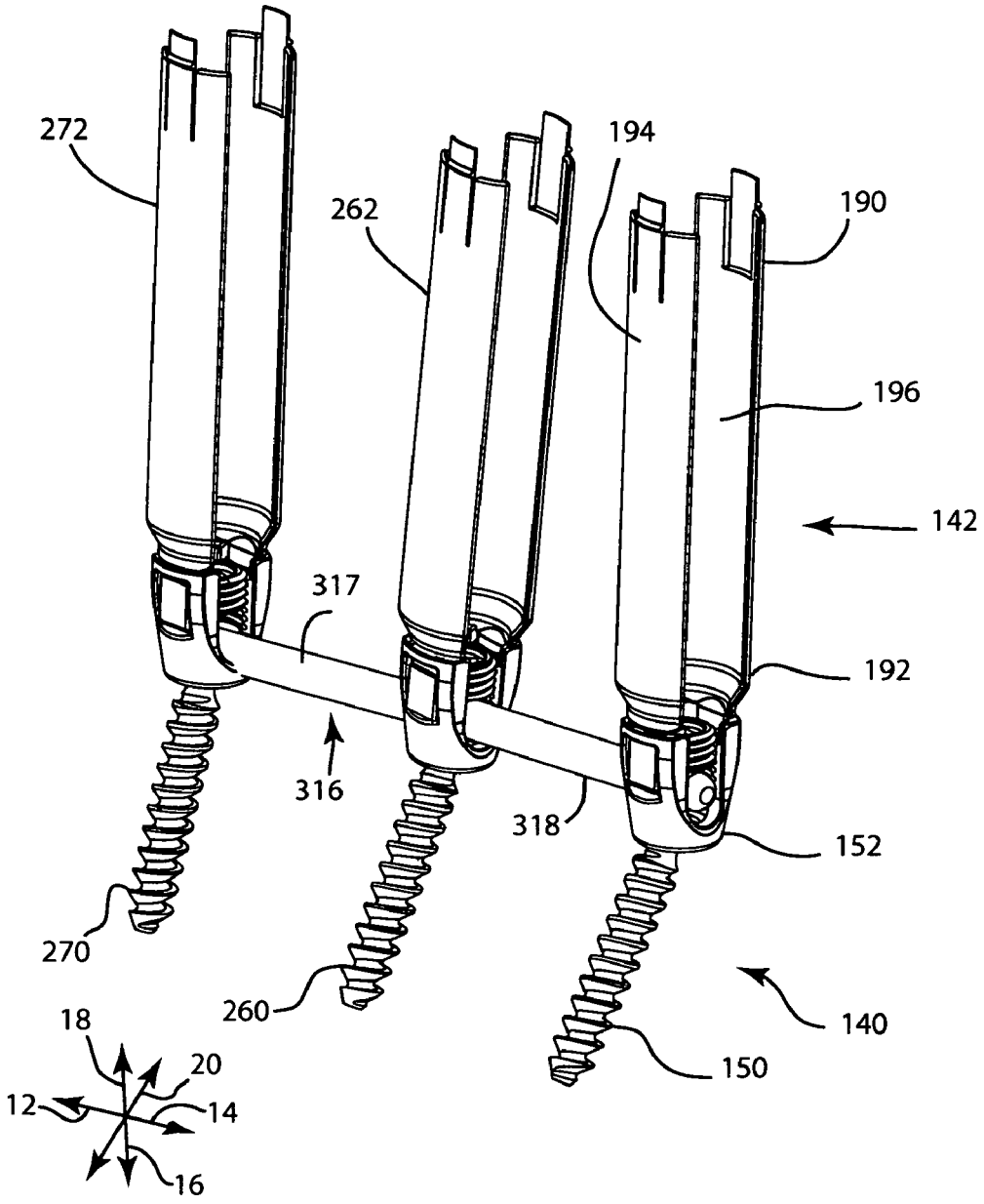
FIG. 22 is a perspective view of the pedicle screws, cages, set screws, and cannulas of FIG. 11, with the abutment members removed to permit removal of the cannulas from the cages.

Referring to FIG. 22, a perspective view illustrates the fully assembled posterior spinal fusion system including the connecting elements 140, 260, 270 and the rod 316, with the cannulas 142, 262, 272 still secured to the cages 152 of the connecting elements 140, 260, 270, but with the abutment members 144, 264, 274 removed from the cannulas 142, 262, 272. The abutment members 144, 264, 274 may be removed from the cannulas 142, 262, 272 by squeezing the proximal tabs 202 of each cannula 142, 262, 272 together, for example, with the thumb and forefinger of a hand. The locking ridges 206 are thereby moved into alignment with the arcuate slots 218 of the abutment members 144, 264, 274 so that the abutment members 144, 264, 274 can be withdrawn along the posterior direction 18 from the corresponding cannulas 142, 262, 272, respectively.

As mentioned previously, once the abutment members 144, 264, 274 have been removed, the blades 194, 196 of each cannula 142, 262, 272 may be pivoted into the unlocked configuration. The distal tabs 204 may then be withdrawn from the slots 174 of the arms 172 of the cages 152, and out of the patient's body. Then, the incisions made to accommodate the cannulas 142, 262, 272 may be closed and treated through the use of methods known in the art.

Figure 23:
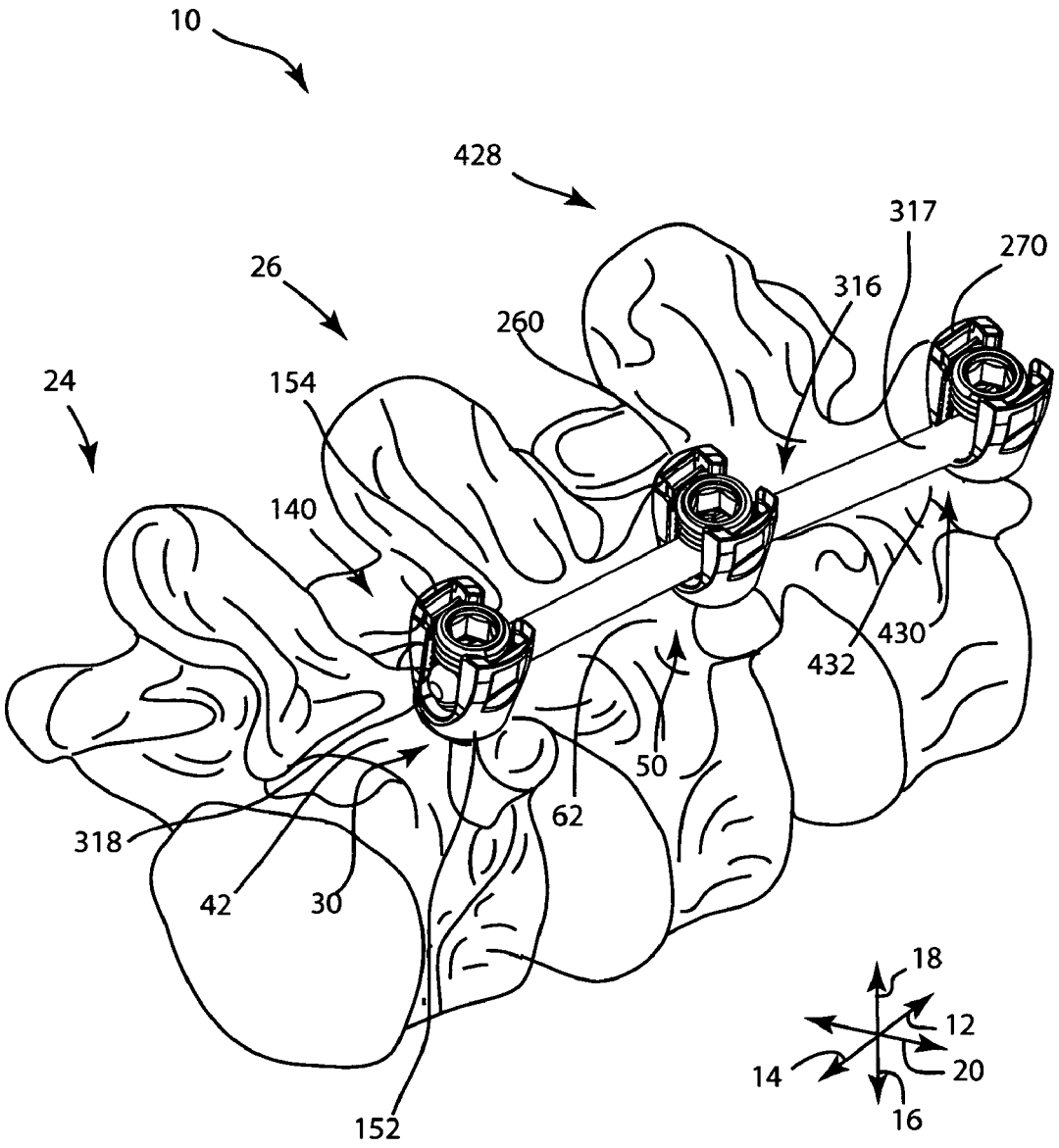
FIG. 23 is a perspective view of three adjacent vertebrae of the spine, with the rod secured to the pedicle screws to provide posterior spinal fusion.
Figure 24:
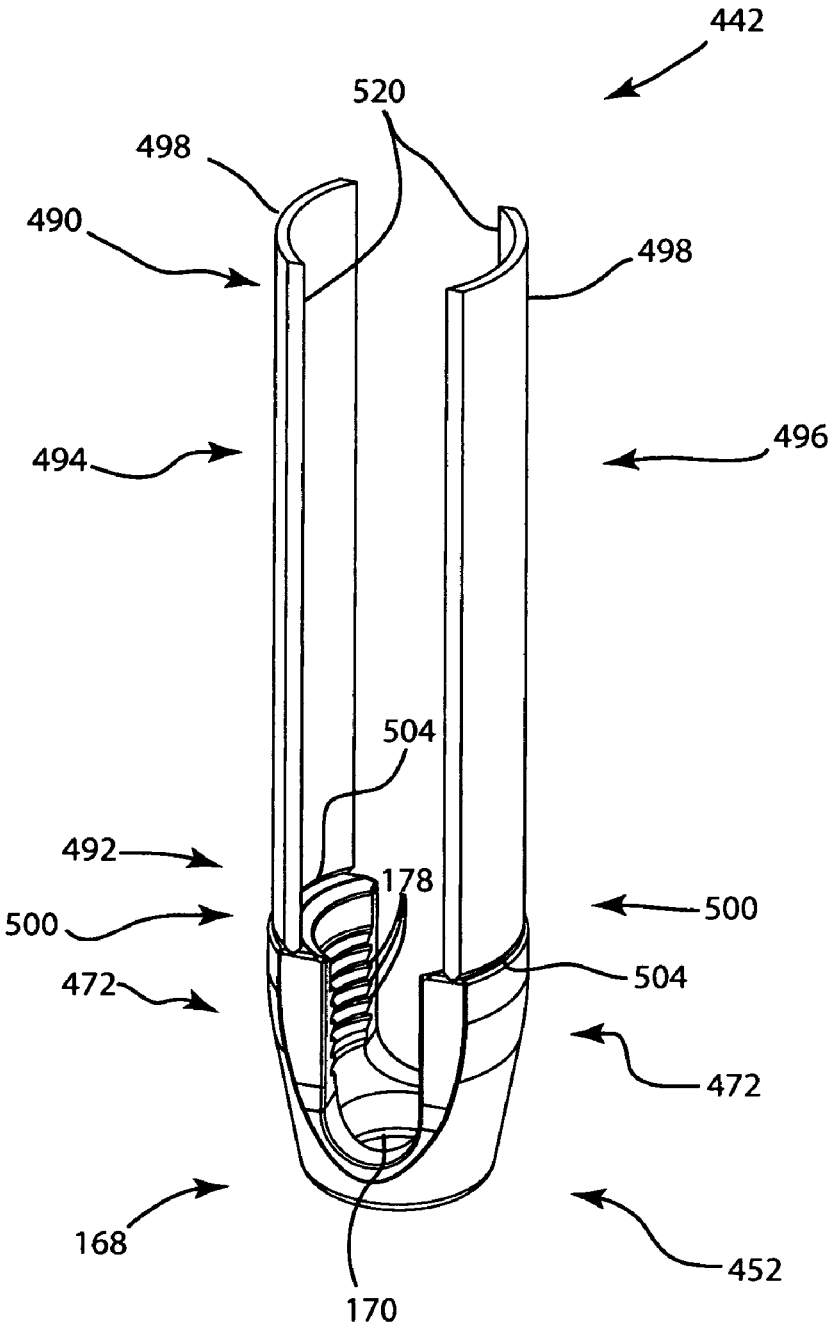
FIG. 24 is a perspective view of a cannula and cage according to one alternative embodiment of the invention, in which the cannula is secured to the cage by two frangible couplings.

Referring to FIG. 23, a perspective view illustrates the completed posterior spinal fusion system. In addition to the first and second vertebrae 24, 26, FIG. 23 illustrates a third vertebra 428 superior to the second vertebra 26. The third vertebra 428 has features similar to those set forth in the description of the first and second vertebrae 24, 26. Most pertinently, the third vertebra 428 has pedicles 430 with saddle points 432.

As shown, the pedicle screw 150 of the first connecting element 140 is implanted in the pedicle 30 of the right side of the first vertebra 24, the pedicle screw 150 of the second connecting element 260 is implanted in the pedicle 50 of the right side of the second vertebra 26, and the pedicle screw 150 of the third connecting element 270 is implanted in the pedicle 430 of the right side of the third vertebra 428. The rod 316 passes through the troughs of the cages 152 in a manner that preserves the proper lordosis of the spine 10. The set screws 154 have been rotated into engagement with the cages 152 and tightened to keep the rod 316 in place within the troughs of the cages 152 and to substantially eliminate rotation of the cages 152 relative to their respective vertebrae 24, 26, 428.

The connecting elements 140, 260, 270 thus cooperate with the rod 316 to restrict relative motion of the vertebrae 24, 26, 428 to form a posterior vertebral fusion system. If desired, a similar system may be implanted in the left-side pedicles 30, 50, 430 of the vertebrae 24, 26, 428 through the method set forth previously to provide a bilateral system. Additionally, the present invention is not limited to a three-level fusion system, but may be used to fuse any number of vertebrae together. To fuse more than three vertebrae together, the steps set forth above may simply be repeated for each additional vertebra, and the rod may be inserted through the skin via a first cannula, and then percutaneously inserted through three or more additional cannulas.

A variety of alternative embodiments of the invention may be used in place of the method and components illustrated in FIGS. 1-23. For example, a variety of different connecting elements known in the art may be used in place of the connecting elements 140, 260, 270 shown and described previously. Polyaxially rotatable cages are an optional feature of such connecting elements. Cannulas different from the cannulas 142, 262, 272 set forth above may be used, and need not be formed of multiple separate pieces, but may instead be single piece structures. Such cannulas may have slots that terminate toward their proximal ends.

A variety of different docking elements may be used in place of the distal tabs 204 and the slots 174. Such docking elements may include threaded engagement, collets, pin-and-locking-groove systems, interference fit couplings, snap-fit couplings, and the like. Additionally, a variety of locking mechanisms may be used in place of the proximal tabs 202. Such locking mechanisms may include locking members securable to the proximal ends 190 of the cannulas 142, 262, 272 to interfere with withdrawal of the abutment members 144, 264, 274 therefrom, or locking members movably coupled to the proximal ends 190. Additionally, a wide variety of interfaces may be provided between each cannula 142, 262, 272 and the corresponding abutment member 144, 164, 274 to restrict withdrawal of the abutment members 144, 264, 274 from the cannulas 142, 262, 272.

Furthermore, each of the instruments set forth previously, including the screw insertion tool 230, the fascia clipping tool 280, the rod insertion tool 300, the rod seating tool 320, the rod holding tool 340, and the set screw driver 400, may be replaced with an alternatively configured tool that performs a similar function. The steps recited above need not necessarily be performed in the order provided, but may instead be rearranged, and some steps may be omitted and/or other steps may be added, to provide alternative methods within the scope of the invention.

According to one alternative embodiment of the invention, a connecting element may have a cage pre-attached to a cannula that provides access to the cage. Such an alternative embodiment will be shown and described in greater detail in connection with FIG. 24.

Referring to FIG. 24, a perspective view illustrates a cannula 442 and a cage 452 according to one alternative embodiment of the invention in which the cannula 442 and the cage 452 are initially secured together. The cage 452 may be part of a connecting element like the connecting elements 140, 260, 270 set forth previously. Accordingly, the cage 452 may be polyaxially coupled to a pedicle screw like the pedicle screw 150 of FIG. 7, and may be designed to receive a rod portion 146 like that of FIG. 7. The cage 452 may also receive a set screw 154 like that of FIG. 7 to keep the rod portion 146 in place and restrain pivotal relative motion between the cage 452 and the pedicle screw 150.

As shown in FIG. 24, the cage 452 has a base 168 with an aperture 170 designed to receive the pedicle screw 150. The cage 452 has a pair of arms 472 extending from the base 168. The arms 472 need not have slots 174 or exterior recesses 176 like the arms 172 of the cage 152 of FIG. 7. However, each of the arms 472 does have threads 478 that face inward to receive the set screw 154.

The cannula 442 has a generally tubular shape with a proximal end 490 and a distal end 492. The cannula 442 includes a first blade 494 and a second blade 496 positioned opposite the first blade 494. Each of the blades 494, 496 has a proximal end 498 that is substantially free, and a distal end 500 pre-attached to the corresponding arm 472 of the cage 452. In the embodiment of FIG. 24, the distal ends 500 are formed as a single piece with the arms 472, and are separated from the arms 472 by frangible portions 504 of the distal ends 500. The cannula 442 has a pair of slots 520 positioned opposite to each other to permit percutaneous insertion of the rod 316 therein, as described in connection with the previous embodiment.

Each frangible portion 504 may take the form of a necked-down region designed to fracture in response to application of a certain pre-established threshold linear force or angular moment. More precisely, each frangible portion 504 may fracture in response to force tending to tilt the blades 494, 496 to push the proximal ends 498 inward, toward the axis of the cannula 442. Thus, the frangible portions 504 define a frangible coupling between the cannula 442 and the cage 452.

In use, the cannula 442 and the cage 452 may be used in a manner similar to that set forth in FIGS. 1-23. However, the cannula 442 and the cage 452 need not be secured together, since they are formed as a single piece. Additionally, no abutment member may be necessary, although an abutment member (not shown) somewhat similar to the abutment member 144 may optionally be used to maintain the proper relative displacement of the blades 494, 496 during use. After implantation of the rod 316, removal of the blades 494, 496 from the cage 452 may be accomplished by tilting the blades 494, 496 inward as described previously to fracture the frangible portions 504, thereby permitting separation of the blades 494, 496 from the cage 452.

According to other alternative embodiments (not shown), blades may be pre-attached to a cage in a manner that does not require the blades to be formed as a single piece with the cage. For example, the blades may be welded, mechanically fastened, or otherwise pre-attached to the cage. Such embodiments may optionally have frangible portions. Alternatively, the blades may be removable in other ways, such as via removal of a mechanical fastener.

The foregoing description discloses a number of different elements that may be combined in various ways to provide a number of alternative implantable systems. Although the foregoing examples relate to implantation of a posterior spinal fusion system, the present invention may be applied to a wide variety of implants, within and outside the orthopedic area.

The present invention may be embodied in other specific forms without departing from its spirit or essential characteristics. It is appreciated that various features of the systems and methods described above can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

[1. A system for providing access to a spine of a patient, the system comprising:

a first connecting element implantable in a first vertebra of a spine; and a first cannula adapted to receive at least a portion of a spinal fusion rod therealong, the first cannula comprising:

a first blade; and a second blade discrete from the first blade;

wherein the first and second blades are configured to be assembled together substantially parallel to each other and mated with the first connecting element, without being directly connected to one another, in order to provide the first cannula such that the first cannula has a distal end terminating at the connecting element, whereby the first cannula provides access to the spine when the first connecting element is implanted in the first vertebra of the spine; and wherein the first and second blades are independently detachable from the first connecting element such that the first and second blades are independently removable from the patient.]

[2. The system of claim 1, wherein the connecting element comprises a pedicle screw implantable in a pedicle of the first vertebra, and a cage polyaxially movable with respect to the pedicle screw.]

[3. The system of claim 1, wherein the first and second blades are configured to be disassembled from one another without removing the distal end from within the patient.]

[4. The system of claim 3, wherein each of the first and second blades comprises a locked configuration, in which the blade is secured to the connecting element, and an unlocked configuration, in which the blade is removable from the connecting element, wherein each of the first and second blades is movable between the locked and unlocked configurations in response to rotation of the blade with respect to the connecting element.]

[5. The system of claim 4, wherein each of the first and second blades is movable between the locked and unlocked configurations in response to rotation of the blade about an axis substantially perpendicular to a longitudinal axis of the first cannula.]

[6. The system of claim 1, further comprising an abutment member configured to engage the first and second blades to restrict relative motion between the first and second blades.]

[7. The system of claim 6, wherein the abutment member is lockable with respect to the first and second blades by a locking mechanism that restricts withdrawal of the abutment member from the first and second blades.]

[8. The system of claim 7, wherein the locking mechanism comprises a plurality of proximal tabs of the first and second blades, wherein the proximal tabs are bendable to permit withdrawal of the abutment member from the first and second blades.]

[9. The system of claim 1, further comprising an abutment member encircling at least a portion of the first cannula to abut an exterior skin surface of the patient, wherein the abutment member is movable along the first cannula to define a variable subcutaneous length of the first cannula.]

[10. The system of claim 9, wherein the abutment member is shaped such that a combined length of the first cannula and the abutment member does not change in response to motion of the abutment member along the first cannula.]

[11. The system of claim 1, wherein the first and second blades are shaped such that, when positioned to define the first cannula, the first and second blades provide a first slot in a side wall of the first cannula.]

[12. The system of claim 11, wherein the first and second blades are further shaped such that, when positioned to define the first cannula, the first and second blades provide a second slot in the side wall, wherein the second slot is arranged with respect to the first slot to permit passage of a rod through the first cannula along a direction transverse to a longitudinal axis of the first cannula.]

[13. The system of claim 12, wherein the distal end is insertable into the patient proximate the spine such that each of the first and second slots extends unbroken along an entire subcutaneous length of the cannula.]

[14. The system of claim 1, further comprising a second cannula securable to a second connecting element implantable in a second vertebra of the spine, and a third cannula securable to a third connecting element implantable in a third vertebra of the spine, wherein the first, second, and third cannulas cooperate to facilitate attachment of a rod to the first, second, and third connecting elements to restrict relative motion of the first, second, and third vertebrae.]

[15. The system of claim 1, wherein the first and second blades have arcuate profiles, whereby the first cannula is defined by a partially cylindrical shape.]

[16. The system of claim 1, wherein the first and second blades each have a distal end including a tab insertable into a corresponding slot of the first connecting element.]

[17. The system of claim 1, further comprising an abutment member configured to prevent the first and second blades from becoming disconnected from the first connecting element.]

[18. A system for providing access to a spine of a patient, the system comprising:

a cannula adapted to receive at least a portion of a spinal fusion rod therealong, the cannula comprising a proximal end and a distal end insertable into the patient proximate the spine, the distal end comprising a docking element discrete from and securable to a connecting element implantable in a first vertebra of the spine;

wherein the docking element is receivable by the connecting element in both a docked configuration and an undocked configuration, the distal end being secured to the connecting element in the docked configuration, and the distal end being received by and removable from the connecting element in the undocked configuration, and wherein the docking element is movable between the docked and undocked configurations in response to rotation about an axis substantially perpendicular to a longitudinal axis of the cannula.]

[19. The system of claim 18, wherein the connecting element comprises a pedicle screw implantable in a pedicle of the first vertebra, and a cage polyaxially movable with respect to the pedicle screw, wherein the docking element is configured to dock with the cage.]

[20. The system of claim 19, wherein the cannula comprises:

a first blade; and a second blade discrete from the first blade;

wherein the first and second blades are positionable substantially parallel to each other to provide the first cannula;

wherein each of the first and second blades comprises a locked configuration, in which the blade is secured to the connecting element, and an unlocked configuration, in which the blade is removable from the connecting element.]

[21. The system of claim 18, wherein the docking element includes a plurality of tabs, each of the first and second blades comprising at least one of the tabs at a distal end thereof, the tabs enabling rotation of the blades between the locked configuration and the unlocked configuration.]

[22. The system of claim 18, further comprising an abutment member configured to engage the first and second blades to restrict relative motion between the first and second blades to restrict motion of the blades to the unlocked configuration.]

[23. The system of claim 22, wherein the abutment member is lockable with respect to the first and second blades by a locking mechanism that restricts withdrawal of the abutment member from the first and second blades.]

[24. The system of claim 23, wherein the locking mechanism comprises a proximal tab of each of the first and second blades, wherein the proximal tabs are bendable to permit withdrawal of the abutment member from the first and second blades.]

[25. A system for providing access to a spine of a patient, the system comprising:

a cannula adapted to receive at least a portion of a spinal fusion rod therealong, the cannula comprising a distal end insertable into the patient proximate the spine and securable to a connecting element implantable in a first vertebra of the spine, the cannula further comprising a proximal end and a longitudinal axis extending between the proximal and distal ends; and an abutment member encircling at least a portion of the cannula and adapted to abut an outward facing surface of skin of the patient, the entire length of the abutment member along the longitudinal axis of the cannula being disposed between the proximal and distal ends of the cannula, wherein the abutment member is adapted to move along the cannula from the proximal end to the distal end such that the abutment member can be moved to a position abutting the outward facing surface of skin when the distal end of the cannula is secured to the connecting element, whereby a variable subcutaneous length of the cannula is defined, and wherein a combined length of the cannula and the abutment member does not change in response to motion of the abutment member along the cannula.]

[26. The system of claim 25, wherein the cannula comprises:

a first blade; and a second blade discrete from the first blade;

wherein the first and second blades are positionable substantially parallel to each other to provide the cannula.]

[27. The system of claim 26, wherein the abutment member is configured to engage the first and second blades to restrict relative motion between the first and second blades.]

[28. The system of claim 25, wherein the abutment member is lockable with respect to the cannula by a locking mechanism that restricts withdrawal of the abutment member from the cannula.]

[29. The system of claim 28, wherein the locking mechanism comprises a plurality of proximal tabs of the cannula, wherein the proximal tabs are bendable to permit withdrawal of the abutment member from the cannula.]

[30. The system of claim 25, wherein the cannula comprises a first slot extending longitudinally along a side wall of the cannula.]

[31. The system of claim 25, wherein the cannula comprises a docking element that couples the cannula to a connecting element implantable in a vertebra of the spine, wherein the docking element comprises a frangible coupling configured to fracture in response to application of a threshold force against the frangible coupling to permit removal of the distal end from the connecting element.]

[32. A system for providing access to a spine of a patient, the system comprising:

a cannula comprising:

a first component; and a second component discrete from the first component; and an abutment member;

wherein the first and second components are configured to be assembled to a connecting element implantable in a first vertebra of the spine, wherein each of the first and second components has a distal end receivable in the connecting element in a receiving position and a locked position, each of the first and second components being movable between the receiving position and the locked position in response to rotation about an axis substantially perpendicular to a longitudinal axis of the cannula, wherein the abutment member configured to engage the first and second components to restrict relative motion between the first and second components, and wherein the abutment member is lockable with respect to the first and second components by a locking mechanism that restricts withdrawal of the abutment member from the first and second blades.]

[33. The system of claim 32, wherein the first component comprises a first blade, and the second component comprises a second blade, wherein the first and second blades are positionable substantially parallel to each other to provide the cannula.]

[34. The system of claim 33, wherein the distal end comprises a docking element securable to a connecting element implantable in a first vertebra of the spine, wherein each of the first and second blades is secured to the connecting element in the locked position and received within but removable from the connecting element in the receiving position.]

[35. The system of claim 32, wherein the locking mechanism comprises a plurality of proximal tabs of the first and second components, wherein the proximal tabs are bendable to permit withdrawal of the abutment member from the first and second components.]

[36. The system of claim 32, wherein the first and second components have arcuate surfaces, whereby the cannula is defined by a partially cylindrical shape.]

[37. A system for providing access to a spine of a patient, the system comprising:

a cannula adapted to receive at least a portion of a spinal fusion rod therealong, the cannula having a longitudinal axis and comprising a distal end insertable into the patient proximate the spine, and a proximal end, the distal end comprising a docking element securable to a connecting element implantable in a first vertebra of the spine; and an abutment member encircling at least a portion of the cannula, the abutment member having an abutment surface substantially normal to the longitudinal axis, the abutment surface adapted to abut an exterior skin surface of the patient, wherein the abutment member is adapted to move along the cannula from the proximal end to the distal end such that the abutment member can be moved to a position wherein the abutment surface abuts the exterior skin surface when the docking element is secured to the connecting element implanted in the first vertebra of the spine, whereby a variable subcutaneous length of the cannula is defined.]

[38. The system of claim 37, wherein the connecting element comprises a pedicle screw implantable in a pedicle of the first vertebra, and a cage polyaxially movable with respect to the pedicle screw.]

[39. The system of claim 37, wherein the abutment member is lockable with respect to the cannula by a locking mechanism that restricts withdrawal of the abutment member from the cannula.]

[40. The system of claim 39, wherein the locking mechanism comprises a plurality of proximal tabs of the cannula, wherein the proximal tabs are bendable to permit withdrawal of the abutment member from the cannula.]

[41. The system of claim 37, wherein the abutment member is shaped such that a combined length of the cannula and the abutment member does not change in response to motion of the abutment member along the cannula.]

[42. The system of claim 37, wherein the cannula further comprises a first slot portion formed in a side wall of the cannula.]

[43. The system of claim 42, wherein the cannula further comprises a second slot portion formed in the side wall, wherein the second slot is arranged with respect to the first slot to permit passage of a rod through the cannula along a direction transverse to the longitudinal axis of the cannula.]

[44. The system of claim 43, wherein the distal end is insertable into the patient proximate the spine such that each of the first and second slots extends unbroken along the entire subcutaneous length.]

[45. The system of claim 37, wherein the docking element comprises a frangible coupling configured to fracture in response to application of a threshold force against the frangible coupling to permit removal of the distal end from the connecting element.]

[46. The system of claim 37, wherein the cannula comprises:

a first blade; and a second blade discrete from the first blade;

wherein the first and second blades are positionable substantially parallel to each other to provide the cannula, and wherein the abutment member is configured to engage the first and second blades to restrict relative motion between the first and second blades.]

[47. A system for providing access to a spine of a patient, the system comprising:

a cannula adapted to receive at least a portion of a spinal fusion rod therealong, the cannula comprising a distal end insertable into the patient proximate the spine and securable to a connecting element implantable in a first vertebra of the spine, the cannula further comprising a proximal end and a first slot extending longitudinally between the distal and proximal ends; and an abutment member encircling at least a portion of the cannula, the abutment member having an abutment surface extending substantially laterally from an outer surface of the cannula, the abutment surface adapted to abut an exterior skin surface of the patient, wherein the abutment member is adapted to move along the cannula from the proximal end to the distal end such that the abutment member can be moved to a position wherein the abutment surface abuts the exterior skin surface when the distal end of the cannula is secured to the connecting element implanted in the first vertebra of the spine, whereby a variable subcutaneous length of the cannula is defined.]

[48. The system of claim 47, wherein the abutment member is lockable with respect to the cannula by a locking mechanism that restricts withdrawal of the abutment member from the cannula.]

[49. The system of claim 48, wherein the locking mechanism comprises a plurality of proximal tabs of the cannula, wherein the proximal tabs are bendable to permit withdrawal of the abutment member from the cannula.]

[50. The system of claim 47, wherein the abutment member is shaped such that a combined length of the cannula and the abutment member does not change in response to motion of the abutment member along the cannula.]

[51. The system of claim 47, wherein the cannula further comprises a second slot portion formed in the side wall, wherein the second slot is arranged with respect to the first slot to permit passage of a rod through the cannula along a direction transverse to a longitudinal axis of the cannula.]

[52. The system of claim 51, wherein the distal end is insertable into the patient proximate the spine such that each of the first and second slots extends unbroken along the entire subcutaneous length.]

[53. The system of claim 47, wherein the cannula comprises a docking element that couples the cannula to a connecting element implantable in a vertebra of the spine, wherein the docking element comprises a frangible coupling configured to fracture in response to application of a threshold force against the frangible coupling to permit removal of the distal end from the connecting element.]

[54. The system of claim 47, wherein the cannula comprises:

a first blade; and a second blade discrete from the first blade;

wherein the first and second blades are positionable substantially parallel to each other to provide the cannula, and wherein the abutment member is configured to engage the first and second blades to restrict relative motion between the first and second blades.]

*55. A system for providing access to a spine of a patient, the system comprising:*

*a connecting element implantable in a vertebra of the spine and configured to receive an implant;*

*a first blade and a second blade, each of the first and second blades having a distal end and a proximal end, the distal end of each of the first and second blades forming a docking element that secures the respective blade to the connecting element such that the first and second blades extend proximally from the connecting element along an axis positioned between the first and second blades, the first and second blades being dimensioned such that the proximal end of each of the first and second blades extends proximally through a first incision in the skin of the patient while the distal end of the respective blade is secured to the connecting element when the connecting element is implanted in the vertebra of the spine; and*

*a stabilization member configured to engage the first and second blades so as to maintain the first and second blades in a substantially parallel relationship, wherein the stabilization member is lockable with respect to each of the first and second blades by a respective locking mechanism that restricts withdrawal of the stabilization member from the first and second blades, the locking mechanism of each of the first and second blades comprising a proximal tab at the proximal end of each of the first and second blades;*

*wherein each of the first and second blades are detachable from the connecting element by tilting the respective blade to move the proximal end of the respective blade laterally with respect to the axis.*

*56. The system of claim 55, wherein the connecting element comprises a pedicle screw having a cage coupled thereto for receiving the implant, the implant being a spinal fusion rod.*

*57. The system of claim 56, further comprising the spinal fusion rod.*

*58. The system of claim 56, wherein the cage is polyaxially coupled to the pedicle screw, the cage being configured to receive the spinal fusion rod and a set screw, such that the set screw keeps the spinal fusion rod in place in the cage and restrains pivotal relative motion between the cage and the pedicle screw, the system further comprising the set screw.*

*59. The system of claim 55, wherein the stabilization member is movable along the first and second blades to define a variable subcutaneous length of the first and second blades.*

*60. The system of claim 55, wherein the stabilization member has a C-shaped wall partially surrounding a central opening and defining an open side.*

*61. The system of claim 55, wherein the first and second blades are integrally joined to the connecting element by a respective frangible portion connecting the distal end of the respective first and second blade with the connecting element, each of the frangible portions being adapted to be fractured in response to a threshold force tending to tilt the respective blade with respect to the axis.*

*62. The system of claim 61, wherein each of the frangible portions comprises a necked-down region designed to fracture in response to application of the threshold force.*

*63. The system of claim 55, wherein the docking element formed by the distal end of each of the first and second blades is discrete from and securable to the connecting element, such that the first and second blades are independently securable to and independently removable from the connecting element.*

*64. The system of claim 63, wherein each of the first and second blades comprises a distal tab forming the respective docking element, each of the distal tabs being insertable through a respective slot in the connecting element.*

*65. The system of claim 55, wherein each of the first and second blades are detachable from the connecting element by tilting the respective blade to move the proximal end of the respective blade inwardly toward the axis.*

*66. The system of claim 55, wherein the first and second blades have arcuate profiles.*

*67. The system of claim 55, further comprising:*

*a second connecting element implantable in a second vertebra of the spine and configured to receive the implant;*

*a third blade and a fourth blade, each of the third and fourth blades having a distal end and a proximal end, the distal end of each of the third and fourth blades forming a docking element that secures the respective blade to the second connecting element such that the third and fourth blades extend proximally from the second connecting element along a second axis positioned between the third and fourth blades, the third and fourth blades being dimensioned such that the proximal end of each of the third and fourth blades extends proximally through a second incision in the skin of the patient while the distal end of the respective blade is secured to the second connecting element when the second connecting element is implanted in the second vertebra of the spine;*

*wherein each of the third and fourth blades are detachable from the second connecting element by tilting the respective blade to move the proximal end of the respective blade laterally with respect to the second axis.*

*68. A method for providing access to a spine of a patient, the method comprising:*

*implanting a connecting element through an incision in the skin of the patient and into a vertebra of the spine with a first blade and a second blade secured to the connecting element so that the first and second blades extend proximally from the implanted connecting element through the first incision, a distal end of each of the first and second blades forming a docking element that secures the respective blade to the connecting element such that the first and second blades extend proximally from the connecting element along an axis positioned between the first and second blades;*

*maintaining the first and second blades in a substantially parallel relationship with a stabilization member engaged with the first and second blades, the stabilization member being lockable with respect to each of the first and second blades by a respective locking mechanism that restricts withdrawal of the stabilization member from the first and second blades, the locking mechanism of each of the first and second blades comprising a proximal tab at a proximal end of each of the first and second blades;*

*moving an implant into engagement with the implanted connecting element through a passageway defined between the first and second blades;*

*detaching the first and second blades from the connecting element by tilting each of the first and second blades to move the proximal end of the respective blade laterally with respect to the axis; and*

*removing the first and second blades from the body of the patient while the connecting element remains implanted in the vertebra.*

*69. The method of claim 68, wherein the connecting element comprises a pedicle screw having a cage coupled thereto for receiving the implant, the implant being a spinal fusion rod.*

*70. The method of claim 68, wherein the step of detaching the first and second blades from the connecting element by tilting each of the first and second blades comprises tilting each of the first and second blades so as to fracture a respective frangible portion integrally joining the connecting element with the respective distal end of the first and second blade.*

*71. The method of claim 68, wherein the step of detaching the first and second blades from the connecting element by tilting each of the first and second blades comprises tilting each of the first and second blades to move the proximal end of the respective blade inwardly toward the axis.*

* * * * *